United States Patent
Xie et al.

(10) Patent No.: US 12,397,049 B2
(45) Date of Patent: Aug. 26, 2025

(54) VIRAL VECTOR DELIVERY SYSTEM FOR BOTH RESPIRATORY AND DIGESTIVE TRACTS OF PIGS AND APPLICATION THEREOF

(71) Applicants: JIANGSU ACADEMY OF AGRICULTURAL SCIENCES, Nanjing (CN); SNU R&DB FOUNDATION, Seoul (KR); GUOTAI (TAIZHOU) CENTER OF TECHNOLOGY INNOVATION FOR VETERINARY BIOLOGICALS, TAIZHOU, Taizhou (CN)

(72) Inventors: Xing Xie, Nanjing (CN); Zhixin Feng, Nanjing (CN); Daesub Song, Seoul (KR); Rong Chen, Nanjing (CN); Fei Hao, Nanjing (CN); Lulu Xu, Nanjing (CN); Minjoo Yeom, Seoul (KR); Jongwoo Lim, Seoul (KR); Lei Zhang, Nanjing (CN); Yuan Gan, Nanjing (CN); Long Zhao, Nanjing (CN); Wenliang Li, Nanjing (CN); Qiyan Xiong, Nanjing (CN); Yongjie Liu, Nanjing (CN); Beibei Liu, Nanjing (CN); Yanfei Yu, Nanjing (CN); Yun Bai, Nanjing (CN); Guoqing Shao, Nanjing (CN)

(73) Assignees: JIANGSU ACADEMY OF AGRICULTURAL SCIENCES, Nanjing (CN); SNU R&DB FOUNDATION, Seoul (KR); GUOTAI (TAIZHOU) CENTER OF TECHNOLOGY INNOVATION FOR VETERINARY BIOLOGICALS, TAIZHOU, Taizhou (CN)

( * ) Notice: Subject to any disclaimer, the term of this patent is extended or adjusted under 35 U.S.C. 154(b) by 0 days.

(21) Appl. No.: 19/012,978

(22) Filed: Jan. 8, 2025

(65) Prior Publication Data

US 2025/0134983 A1    May 1, 2025

Related U.S. Application Data

(63) Continuation of application No. PCT/CN2023/134284, filed on Nov. 27, 2023.

(30) Foreign Application Priority Data

Jun. 30, 2023   (CN) .................... 202310795095.X

(51) Int. Cl.
    *A61K 39/125*   (2006.01)
    *A61K 39/00*    (2006.01)
    (Continued)

(52) U.S. Cl.
    CPC .............. *A61K 39/125* (2013.01); *C12N 7/00* (2013.01); *C12N 15/86* (2013.01); *C12N 15/88* (2013.01);
    (Continued)

(58) Field of Classification Search
    None
    See application file for complete search history.

(56) References Cited

FOREIGN PATENT DOCUMENTS

| CN | 107338225 A | 11/2017 |
| CN | 110468155 A | 11/2019 |

(Continued)

OTHER PUBLICATIONS

English translation of Long et al. (CN112899310) published Jun. 4, 2021.*

(Continued)

*Primary Examiner* — Shanon A. Foley
(74) *Attorney, Agent, or Firm* — Bayramoglu Law Offices LLC

(57) ABSTRACT

A viral vector delivery system for both respiratory and digestive tracts of pigs and an application thereof are provided. The viral vector delivery system includes a backbone plasmid and a helper plasmid. The backbone plasmid is produced by inserting a full-length cDNA of porcine enterovirus B (PEVB) into a pUC57 plasmid. The helper plasmid (Continued)

is produced by inserting a green fluorescent protein-coding gene into a plasmid pCAG-T7-polymerase. The viral vector delivery system can be constructed with high efficiency, can quickly cause a cytopathic effect (CPE) after infecting cells, has a viral titer up to $10^{7.75}$ TCID$_{50}$/mL, and can maintain high stability. A pathogenic epitope for the respiratory and digestive tracts of pigs is inserted into the back 1. PEVB-infected PBEC cells
2. Uninfected PBEC cells 1. VP4 protein

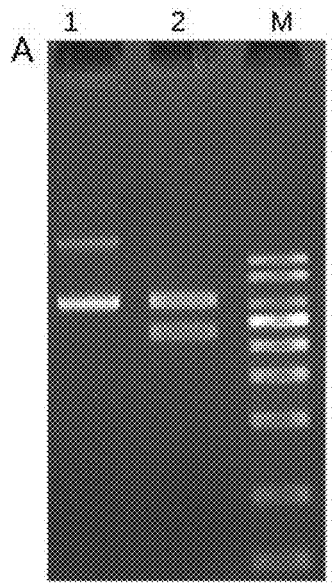 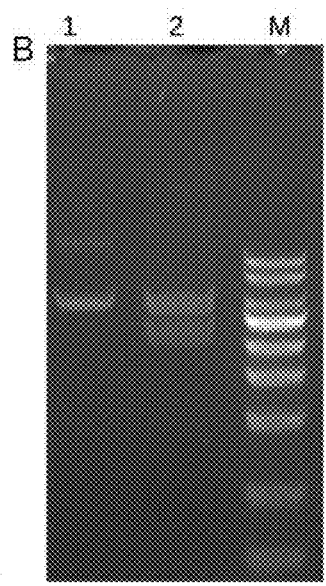 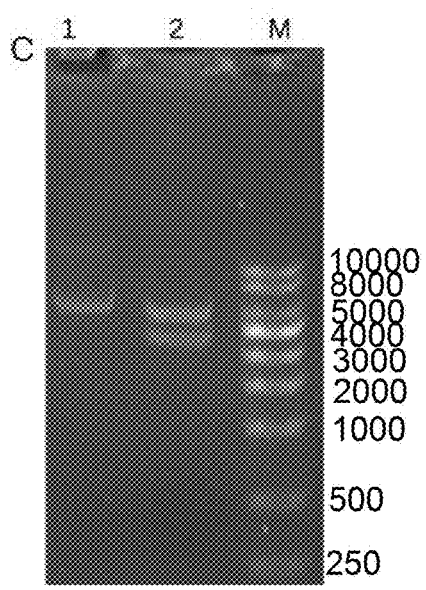
FIG. 12A  FIG. 12B  FIG. 12C
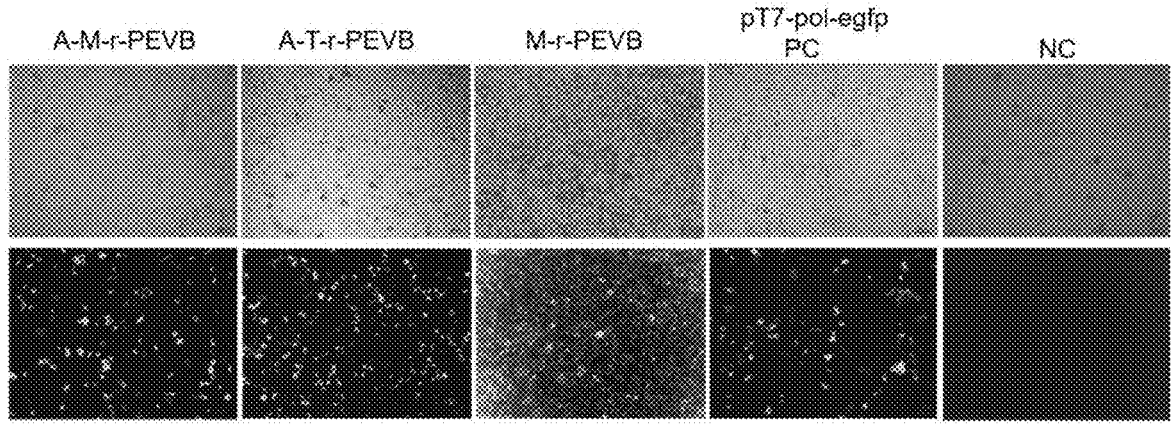
FIG. 13
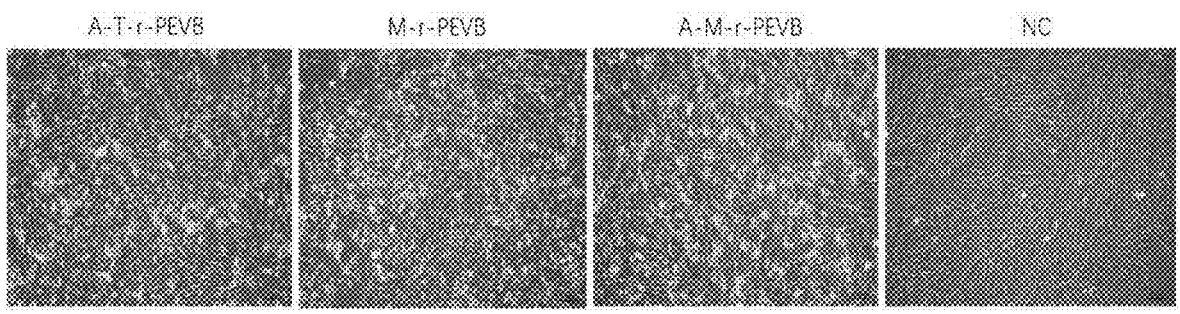
FIG. 14

VIRAL VECTOR DELIVERY SYSTEM FOR BOTH RESPIRATORY AND DIGESTIVE TRACTS OF PIGS AND APPLICATION THEREOF

CROSS REFERENCE TO THE RELATED APPLICATIONS

This application is a continuation application of International Application No. PCT/CN2023/134284, filed on Nov. 27, 2023, which is based upon and claims priority to Chinese Patent Application No. 202310795095.X, filed on Jun. 30, 2023, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBHS015-PKG_Sequence_Listing_20250416.xml, created on Apr. 16, 2025, and is 45,572 bytes in size.

TECHNICAL FIELD

The present disclosure belongs to the field of biotechnologies, specifically relates to a viral vector delivery system for both respiratory and digestive tracts of pigs and an application thereof.

BACKGROUND

Viruses are infectious substances that are associated with a variety of diseases and merely parasitize living organisms. Thus, viruses are often considered extremely harmful to humans and mammals. However, studies have shown that there is a great potential to use viruses as therapeutic agents. As a class of commonly used biological vectors, viral vectors can be used as attractive vaccine platforms due to the ability to induce robust antigen-specific body fluids and cell-mediated immune responses and the high safety. In addition to being used as a tool for delivering foreign genes or genetic materials into organisms or cells, viral vectors are widely used in human and veterinary vaccinations and gene therapy. Although non-viral gene delivery vectors such as liposomes and cationic polymers can also be used in gene therapy and the construction of candidate vaccine strains, viral gene delivery vectors are generally still preferred because viral gene delivery vectors have much higher gene delivery efficiencies in vivo than non-viral gene delivery vectors.

African swine fever virus (ASFV) is a highly infectious pathogen that causes severe hemorrhagic necrosis of the respiratory and digestive tracts of domestic pigs and wild boars. African swine fever caused by ASFV has seriously affected the economy and people's livelihoods. Digestive tract diseases, namely gastrointestinal infections, refer to viral, bacterial, or parasitic infections capable of causing gastroenteritis. That is, the gastrointestinal infections will cause the inflammation of the gastrointestinal tract, including the stomach and small intestine, and lead to symptoms including diarrhea, vomiting, and abdominal pain. Main viral pathogens causing digestive tract symptoms in pigs include porcine epidemic diarrhea virus (PEDV), transmissible gastroenteritis virus (TGEV), porcine deltacoronavirus (PDCOV), etc. The infection of any of these viruses can cause contagious intestinal infections such as vomiting, diarrhea, and dehydration in pigs. Clinically, PDCOV can infect pigs of all ages and mainly causes acute diarrhea and vomiting in suckling pigs, resulting in the rapid dehydration and exhaustion of diseased suckling pigs. Clinically, PDCOV often co-infects with other viruses such as PEDV, TGEV, and porcine reproductive and respiratory syndrome virus (PRRSV), which brings a huge challenge to the prevention and control of enteroviruses because the occurrence of these diseases will greatly reduce the production performance of pigs.

There is a lack of efficient viral vector delivery systems for vaccines to protect the respiratory and digestive tracts of pigs in the prior art.

SUMMARY

An objective of the present disclosure is to provide a viral vector delivery system for both respiratory and digestive tracts of pigs. The system can be constructed with high efficiency, can quickly cause a cytopathic effect (CPE) after infecting cells, has a viral titer up to $10^{7.75}$ TCID$_{50}$/mL, and can maintain high stability.

Another objective of the present disclosure is to provide an application of the viral vector delivery system in construction of a vaccine antigen for respiratory and digestive tracts of pigs. A pathogenic epitope for the respiratory and digestive tracts of pigs is inserted into the backbone plasmid to produce a vaccine antigen, which is non-pathogenic, has high stability and a high viral titer, and allows a prominent immunization effect after being inoculated in pigs.

The objectives of the present disclosure are achieved through the following technical solutions:

A viral vector delivery system for both respiratory and digestive tracts of pigs is provided, including a backbone plasmid and a helper plasmid, where the backbone plasmid is produced by inserting a full-length cDNA of porcine enterovirus B (PEVB) into a pUC57 plasmid; and the helper plasmid is produced by inserting a green fluorescent protein-coding gene into a plasmid pCAG-T7-polymerase.

In the present disclosure, a T7 promoter is inserted at one terminus of the full-length cDNA of the PEVB in the backbone plasmid, and a his-tag and a polyA tail are inserted at the other terminus.

The present disclosure also provides a construction method of the viral vector delivery system, including the following steps: constructing the backbone plasmid and the helper plasmid separately, and co-transfecting the backbone plasmid and the helper plasmid into monkey kidney cells or porcine bronchial epithelial cells.

In the present disclosure, a process for constructing the backbone plasmid is as follows: with a full-length cDNA of a PEVB strain PEV-B-KOR as a template, introducing a T7 promoter at a 5' terminus of the full-length cDNA and a his-tag and a polyA tail at a 3' terminus through polymerase chain reaction (PCR), and inserting into the pUC57 to produce the backbone plasmid.

In the present disclosure, a process for constructing the helper plasmid is as follows: inserting the green fluorescent protein-coding gene into the plasmid pCAG-T7-polymerase to produce the helper plasmid.

In the present disclosure, the backbone plasmid and the helper plasmid are co-transfected into monkey kidney cells veroE6 with a liposome Lipofectamine™ 3000, and viral plaques producing green fluorescence are picked to produce the viral vector delivery system.

The present disclosure also provides an application of the viral vector delivery system in construction of a vaccine antigen for respiratory and digestive tracts of pigs.

In the present disclosure, an epitope-coding gene for a respiratory tract and/or a digestive tract is inserted between a VP4 gene and a 5'UTR gene of the backbone plasmid, and co-transfection is conducted with the helper plasmid using a liposome Lipofectamine™ 3000 into monkey kidney cells veroE6 or porcine bronchial epithelial cells hTERT-PBECs to produce the vaccine antigen.

Compared with the prior art, the present disclosure has the following beneficial effects:

(1) In the present application, for the first time, a T7 promoter is introduced into a full-length PEVB cDNA through PCR to finally produce an infectious clone with the T7 promoter, and the infectious clone is linearly extracted to produce a backbone vector. In addition, a helper plasmid carrying a T7 RNA polymerase and a green fluorescent marker is constructed. The application of the DNA co-transfection strategy eliminates the risk of RNA degradation during transfection in the traditional RNA in vitro transcription method, greatly improves the transfection efficiency, and reduces the time consumption. The system can be constructed with high efficiency and simple operations, and is economical and practical.

(2) In the presence of the helper plasmid, the recombinant porcine enterovirus r-PEVB in the present disclosure can infect immortalized porcine bronchial epithelial cells, and makes the CPE begin at 36 h to 60 h after infection. The r-PEVB can have a viral titer of $10^{7.75}$TCID$_{50}$/mL or more, and exhibits a significantly-higher infection efficiency and titer in porcine bronchial epithelial cells than in African green monkey kidney cells veroE6. A viral titer of the recombinant porcine enterovirus r-PEVB in immortalized porcine bronchial epithelial cells is 0.75 higher than a titer of a wild-type parental viral strain in immortalized porcine bronchial epithelial cells and 0.75 higher than a titer of the wild-type parental viral strain cultured in veroE6, and can remain stable.

(3) A pathogenic epitope for the respiratory and digestive tracts of pigs is inserted into the recombinant porcine enterovirus r-PEVB of the present disclosure to produce a vaccine antigen, which is non-pathogenic, has high stability and a high viral titer, and allows a prominent immunization effect after being inoculated in pigs. Therefore, the viral vector delivery system of the present disclosure can be used for the future research on a variety of candidate vaccine viral strains and multi-vaccines for respiratory and digestive tracts of pigs, and has great theoretical significance and application prospects.

BRIEF DESCRIPTION OF THE DRAWINGS

FIG. 5A is an image of co-transfected cells observed under a white light source and FIG. 5B is an image of co-transfected cells observed under a fluorescence light source;

FIG. 10A is for the recombinant porcine enterovirus r-PEVB, FIG. 10B is for a negative control (NC), and FIG. 10C is for a blank control;

FIGS. 12A-12C show enzyme cleavage identification results of recombinant expression plasmids A-T-r-PEVB, M-r-PEVB, and A-M-r-PEVB, where FIG. 12A shows enzyme cleavage identification results of the recombinant expression plasmid A-T-r-PEVB, where a lane M is for a DL 10000 marker, and lanes 1 and 2 are electropherograms of the recombinant expression plasmid A-T-r-PEVB (uncleaved) and the recombinant expression plasmid A-T-r-PEVB cleaved with EcoRI, respectively; FIG. 12B shows enzyme cleavage identification results of the A-M-r-PEVB, where a lane M is for a DL 10000 marker, and lanes 1 and 2 are electropherograms of the A-M-r-PEVB (uncleaved) and the A-M-r-PEVB cleaved with EcoRI, respectively; and FIG. 12C shows enzyme cleavage identification results of the M-r-PEVB, where a lane M is for a DL 10000 marker, and lanes 1 and 2 are electropherograms of the M-r-PEVB (uncleaved) and the M-r-PEVB cleaved with EcoRI, respectively;

FIG. 13 shows fluorescence identification images of veroE6 co-transfected with each of the recombinant expression plasmids A-T-r-PEVB, M-r-PEVB, and A-M-r-PEVB and the helper plasmid at a mass ratio of 2:1, where the first row shows transfected cells observed under a white light source and the second row shows transfected cells observed under a fluorescence light source; and each row shows fluorescence identification images of veroE6 co-transfected with each of the recombinant expression plasmids A-T-r-PEVB, M-r-PEVB, and A-M-r-PEVB and the helper plasmid and fluorescence identification images of a positive control (PC) and NC sequentially from left to right;

FIG. 14 shows CPEs of hTERT-PBECs infected with P14-generation recombinant viruses A-T-r-PEVB, M-r-PEVB, and A-M-r-PEVB, where CPEs of hTERT-PBECs infected with the recombinant viruses A-T-r-PEVB, M-r-PEVB, and A-M-r-PEVB for 24 h are shown sequentially from left to right, and NC shows a control of hTERT-PBECs not infected with a virus;

FIG. 15 shows IFA identification results of the recombinant virus M-r-PEVB against a *Mycoplasma* hyopneumoniae (Mhp) P97R1 monoclonal antibody and a PEVB VP4 polyclonal antibody, where the left P97-R1 indicates that a corresponding sample is detected with the Mhp P97R1 monoclonal antibody, the left Vp4 indicates that a corresponding sample is detected with the PEVB VP4 polyclonal antibody, NC indicates that a corresponding sample is NC (porcine bronchial epithelial cells hTERT-PBECs not infected with the recombinant porcine enterovirus r-PEVB), the upper DAPI indicates a DAPI channel, RED indicates an RED channel, and MERGE indicates merging;

FIG. 16 shows IFA identification results of the recombinant virus A-T-r-PEVB against an ASFV-positive serum antibody and a rabbit-derived anti-VP4 protein polyclonal antibody, where the left Vp4 indicates that a corresponding sample is detected with the rabbit-derived anti-VP4 protein polyclonal antibody, the left Virus indicates that a corresponding sample is detected with the ASFV-positive serum antibody, NC indicates porcine bronchial epithelial cells hTERT-PBECs not infected with the recombinant porcine enterovirus r-PEVB, the upper DAPI indicates a DAPI channel, RED indicates an RED channel, and MERGE indicates merging;

FIG. 17 shows IFA identification results of the recombinant virus A-M-r-PEVB against an Mhp P97R1 monoclonal antibody, a rabbit-derived anti-VP4 protein polyclonal antibody, and an ASFV-positive serum antibody, where the left P97-R1 indicates that a corresponding sample is detected with the Mhp P97R1 monoclonal antibody, the left Vp4 indicates that a corresponding sample is detected with the rabbit-derived anti-VP4 protein polyclonal antibody, the left Virus indicates that a corresponding sample is detected with the ASFV-positive serum antibody, NC indicates that a corresponding sample is NC (porcine bronchial epithelial cells hTERT-PBECs not infected with the recombinant porcine enterovirus r-PEVB), the upper DAPI indicates a DAPI channel, RED indicates an RED channel, and MERGE indicates merging;

FIG. 18 shows WB identification results of the recombinant viruses A-M-r-PEVB, A-T-r-PEVB, and M-r-PEVB against a rabbit-derived anti-VP4 protein polyclonal antibody, where a lane M is for a protein Marker, and lanes 1 to 4 are for A-M-r-PEVB, A-T-r-PEVB, M-r-PEVB, and NC (hTERT-PBECs not infected with a virus), respectively;

FIG. 19 shows WB identification results of the recombinant viruses A-M-r-PEVB and M-r-PEVB against an Mhp P97R1 monoclonal antibody, where a lane M is for a protein Marker, and lanes 1 to 3 are for A-M-r-PEVB, M-r-PEVB, and NC (hTERT-PBECs not infected with a virus), respectively;

FIG. 20 shows WB identification results of the recombinant viruses A-M-r-PEVB and A-T-r-PEVB against an ASFV-positive serum antibody, where a lane M is for a protein Marker, and lanes 1 to 3 are for A-M-r-PEVB, A-T-r-PEVB, and NC (hTERT-PBECs not infected with a virus), respectively;

FIGS. 21A-21B show HE staining results of ilea collected from dissected pigs infected with the recombinant virus r-PEVB and a parental strain PEV-B-KOR for 14 d, where FIG. 21A shows an HE staining result of an ileum of a pig infected with the recombinant virus r-PEVB and FIG. 21B shows an HE staining result of an ileum of a pig infected with the strain PEV-B-KOR;

FIGS. 22A-22F show serum IgG antibody levels after immunization with the recombinant virus A-T-r-PEVB, specifically the serum IgG antibody levels against the six antigens CD2V-N, P10, P30, P22, P54, and B602L of ASFV, respectively; and a y-coordinate represents an $OD_{450}$ value to reflect a serum IgG antibody level, an x-coordinate represents a blood collection time since the first immunization, Odpi indicates the blood collection on the day of the first immunization, and Negative Control represents an NC group (pigs immunized with a medium);

FIG. 23 shows sIgA expression levels in oral fluids after immunization with the recombinant virus A-T-r-PEVB, where an x-coordinate represents a sampling time since the first immunization, and negative control represents an NC group (oral fluids of pigs immunized with a medium);

FIG. 24 shows secretion levels of inflammatory cytokines on day 14 and 28 after immunization with the recombinant virus A-T-r-PEVB, where a y-coordinate represents a relative cytokine expression level induced by immunization with the recombinant virus A-T-r-PEVB in contrast to pigs immunized with a medium (set as 1), and an x-coordinate represents a sampling time since the first immunization;

FIG. 25 shows T cell typing results of peripheral blood mononuclear cells (PBMCs) from pigs immunized with the recombinant virus A-T-r-PEVB, where in an x-coordinate, "A-T-r-PEVB" and "NC" represent an index of a pig immunized with the recombinant virus A-T-r-PEVB and an index of a pig in an NC group, respectively, and D14 and D28 represent day 14 and day 28 after the first immunization, respectively;

DETAILED DESCRIPTION OF THE EMBODIMENTS

The porcine bronchial epithelial cell line hTERT-PBEC adopted in the present disclosure is published in the CN107338225A, with an accession number CCTCC NO: C201749. The porcine bronchial epithelial cell line can be stably passaged to the 60th generation or more with the characteristics of primary cells retained. Thus, the porcine bronchial epithelial cell line can be used in the research on pathogenic mechanisms of pathogenic infections in porcine respiratory tracts.

The present disclosure is further explained below in conjunction with specific examples. It should be understood that these examples are provided only for a purpose of illustration, and are not intended to limit the protection scope of the present disclosure.

Example 1 Construction Method of a Viral Vector Delivery System for Both Respiratory and Digestive Tracts of Pigs 1. Construction of a Backbone Plasmid and Acquisition of a Linearized Fragment of the Backbone Plasmid 200 μL of a cell culture suspension of a cryopreserved PEVB strain PEV-B-KOR (published in GenBank®, with an NCBI GenBank® accession number of JQ818253) was taken and subjected to total RNA extraction according to operating instructions of a viral RNA/DNA extraction kit (Axygen®, Cat. No: AP-MN-BF-VNA-250, NY, USA). The extracted total RNA was reverse-transcribed with a viral RNA reverse-transcription kit (purchased from Vazyme™, Item No. R223-01) to produce cDNA (SEQ ID NO: 39).

According to enzyme cleavage sites of the virus and a pUC57 Escherichia coli (E. coli) vector plasmid, a forward primer PEntero-F including a T7 promoter and a reverse primer PEntero-R including a polyA tail were designed. With the cDNA as a template and the PEntero-F and PEntero-R as primers, a full-length cDNA of the PEVB strain PEV-B-KOR that was introduced with the T7 promoter at a 5' terminus and a his-tag and a polyA tail at a 3' terminus was amplified. The amplified full-length cDNA and the pUC57 E. coli vector plasmid each were cleaved with EcoRV and then ligated with a T4 DNA ligase, such that the full-length cDNA (7,393 bp) of PEVB (SEQ ID NO: 39), the his-tag, the polyA tail, and the T7 promoter were inserted into the pUC57 plasmid to produce a recombinant plasmid pUC57-PEVB. The recombinant plasmid pUC57-PEVB was introduced into E. coli XL-10 competent cells, and positive clones carrying the recombinant plasmid pUC57-PEVB were selected with an ampicillin-resistant LB plate.

A sequence of the forward primer PEntero-F was as follows: 5'-AATAATACGACTCACTATAGGGT-TAAAACAGCCTGTGGGTTGTTCCCA-3' (SEQ ID NO: 8).

A sequence of the reverse primer PEntero-R was as follows: 5'-AATTTTTTTTTTTTTTTTACACCC-CATCCGGTGGGTGTATTGAATT-3' (SEQ ID NO: 9).

Figure 1:
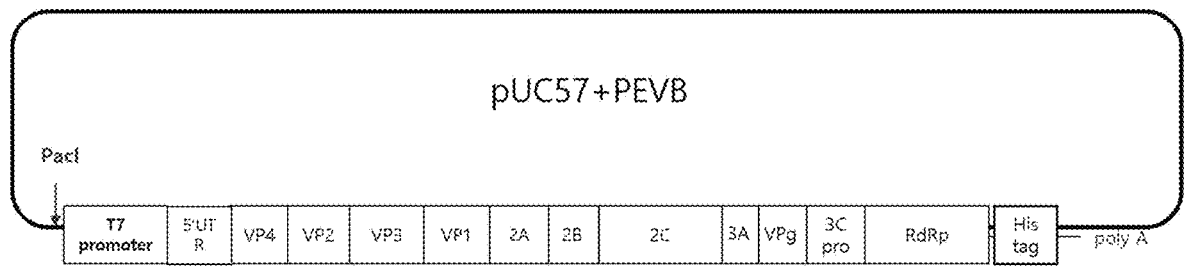
FIG. 1 is a schematic diagram of a structure of a recombinant plasmid pUC57-PEVB.
Figure 2:
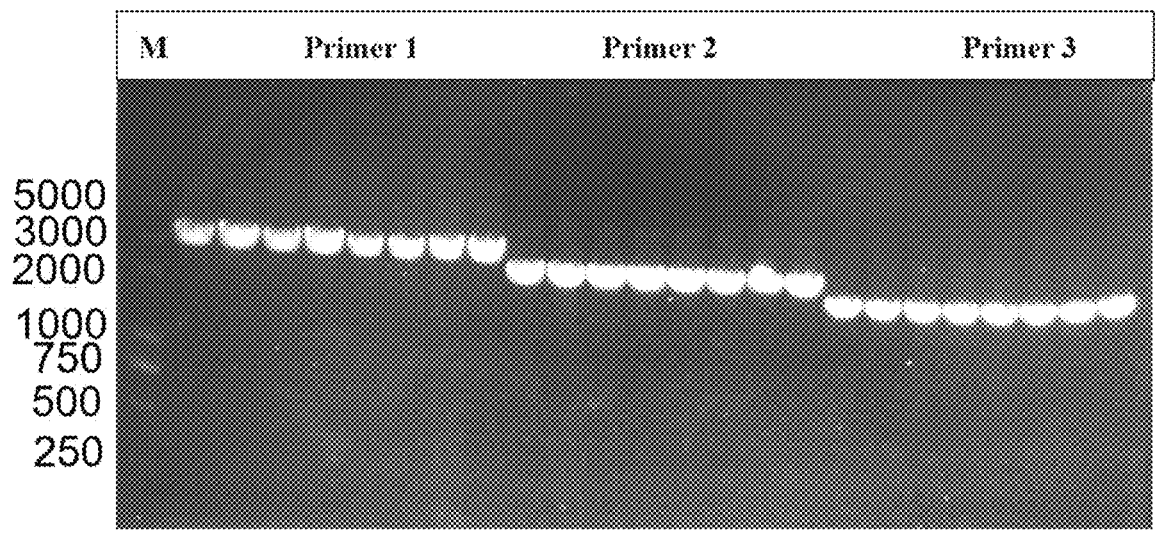
FIG. 2 is an electropherogram of target fragments 1 to 3 resulting from reverse transcription-polymerase chain reaction (RT-PCR) using primers 1, 2, and 3 respectively with RNA of a positive clone 1 carrying the recombinant plasmid pUC57-PEVB as a template, where M represents a DNA Marker DL5000.

A complete genome sequence of the viral strain PEV-B-KOR was divided into target fragments 1, 2, and 3 (details were shown in Table 1). Three pairs of specific primers (as shown in Table 1) were designed with the software Primer Premier 5.0 to amplify the target fragments 1 to 3, respectively. The primers were sent to Nanjing GenScript Biotech Co., Ltd. for synthesis. With RNA of the positive clones carrying the recombinant plasmid pUC57-PEVB as a template, RT-PCR was conducted by a one-step RT-PCR kit (Beijing TransGen Biotech Co., Ltd.) with each pair of specific primers. An RT-PCR system had a total volume of 20 μL, including: 2×R-Mix Buffer: 10 μL, upstream and downstream primers: each 0.5 μL, E-Mix: 0.4 μL, RNA template: 2 μL, and Rnase-free water: making up to 20 μL. An amplification procedure was as follows: reverse-transcription at 45° C. for 30 min; 94° C. for 5 min; 94° C. for 30 s, 55° C. to 60° C. for 30 s (an annealing temperature during amplification for each pair of primers was shown in Table 1), and 72° C. for 2 min, with 35 cycles; and 72° C. for 10 min. The target fragments 1 to 3 each were purified and recovered, then transformed into the E. coli XL-10, and identified and sequenced by colony PCR. According to sequencing results, a viral complete genome sequence produced by splicing target fragments 1 to 3 resulting from RT-PCR with RNA of a positive clone 1 carrying the recombinant plasmid pUC57-PEVB as a template had a sequence homology of 100% with the PEV-B-KOR, indicating that the recombinant plasmid pUC57-PEVB (the backbone plasmid) was successfully constructed. A schematic diagram of a structure of the recombinant plasmid was shown in FIG. 1. PCR identification results of the target fragments 1 to 3 were shown in FIG. 2. The recombinant plasmid pUC57-PEVB in the positive clone 1 was cleaved with PacI, and then recovered with an OMEGA fragment recovery kit to produce a linearized PEVB-containing infectious cloned plasmid (namely, the linearized backbone plasmid), which was named L-pUC57-PEVB.

TABLE 1

Primers for whole genome amplification of the strain PEV-B-KOR

| Target fragment | Primer name | | Primer sequence (5'-3') | Annealing temperature (° C.) |
|---|---|---|---|---|
| 1 (1-3010bp) 3005bp | Primer 1 | F1 | TTAATAATACGAC TCACTATAGGGT (SEQ ID NO: 10) | 56 |
| | | R1 | GGAAGAAGAC TGAAGGGTTT (SEQ ID NO: 11) | |
| 2 (3000-5430bp) 2423bp | Primer 2 | F2 | TGCAGCCAGAT TTAGTGTACCG (SEQ ID NO: 12) | 60 |
| | | R2 | TCATCCCAACT CCAAAGTCCAT (SEQ ID NO: 13) | |
| 3 (5400-7393bp) 1950bp | Primer 3 | F3 | TCTTGGTGTAAT CCAATCTGCAG (SEQ ID NO: 14) | 60 |
| | | R3 | GGCTGCTCTTTT CTCCTAAGTTTT (SEQ ID NO: 15) | |

Figure 3:
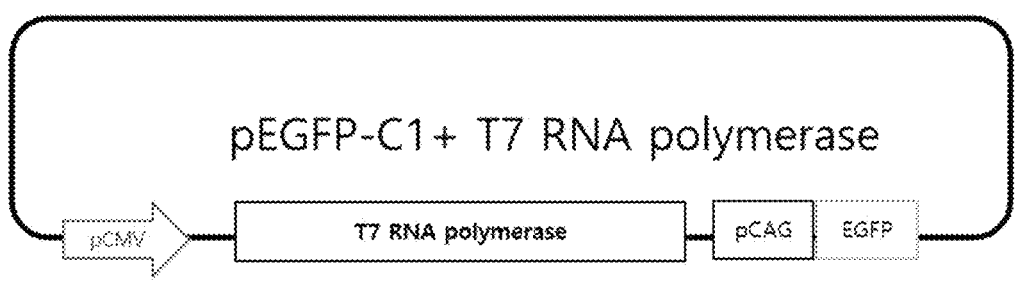
FIG. 3 is schematic diagram of construction of a eukaryotic helper plasmid pCAG-T7 RNA polymerase-EGFP carrying a T7 RNA polymerase-coding gene and a green fluorescent protein-coding gene, where pCAG represents an enhancer in a plasmid pCAG-T7-polymerase and pCMV represents a eukaryotic promoter in the plasmid pCAG-T7-polymerase.

2. Construction of a Helper Plasmid Carrying a T7 RNA Polymerase and a Green Fluorescent Marker With a eukaryotic expression vector plasmid pEGFG-C1 (purchased from Clontech) as a template and E-F and E-R (Table 2) as primers, a green fluorescent protein-coding gene EGFP fragment was amplified. Based on the principle of homologous recombination, the amplified EGFP fragment was inserted into pCAG-T7-polymerase with a ClonExpress® II One Step Cloning Kit (purchased from Vazyme, Item No. Vazyme.C112-01). The pCAG-T7-polymerase included a T7 RNA polymerase-coding gene. A specific method was as follows: The amplified green fluorescent protein-coding gene EGFP fragment was cleaved with Hind/II, and then ligated by a T4 DNA ligase with pCAG-T7-polymerase that was also cleaved with Hind///to produce the eukaryotic helper plasmid carrying the T7 RNA polymerase-coding gene and the green fluorescent protein-coding gene, which was denoted as pCAG-T7 RNA polymerase-EGFP. A schematic diagram of the construction was shown in FIG. 3. A ligation system was as follows: 5×CE II buffer: 4 μL, an enhanced recombinase Exnase II: 2 μL, the amplified green fluorescent protein-coding gene EGFP fragment: 5 μL, the linearized pCAG-T7-polymerase: 5 μL, and ddH$_2$O: 4 μL.

TABLE 2

Primers for construction of the helper plasmid

| Target fragment | Primer name | Primer sequence (5'-3') | Annealing temperature (° C.) |
|---|---|---|---|
| T7 RNA polymerase | T7-pol-F | TCTCATCACTAC CCTACGCAATA (SEQ ID NO: 16) | 56 |
| | T7-pol-R | TCTCGTGATG GGACACTAAC (SEQ ID NO: 17) | |
| Enhancer pCAG | C-F | AAGGGAACTCT TGAGGTTAGAT (SEQ ID NO: 18) | 55 |
| | C-R | ACGATCAAG GGTCCGACT (SEQ ID NO: 19) | |
| Green fluorescent protein-coding gene EGFP | E-F | ctcgacctgcagccc aagcttACATAACTT ACGGTAAATGGCCCG (SEQ ID NO: 20) | 61 |
| | E-R | Gaccatgattacgcc aagcttTAAGATACA TTGATGAGTTTGGAC AAAC (SEQ ID NO: 21) | |

Notes:
In Table 2, a lowercase sequence is a recombinant sequence added at a 5' terminus for homologous recombination, and the underlined indicates the enzyme cleavage site: AAGCTT.

Figure 4:
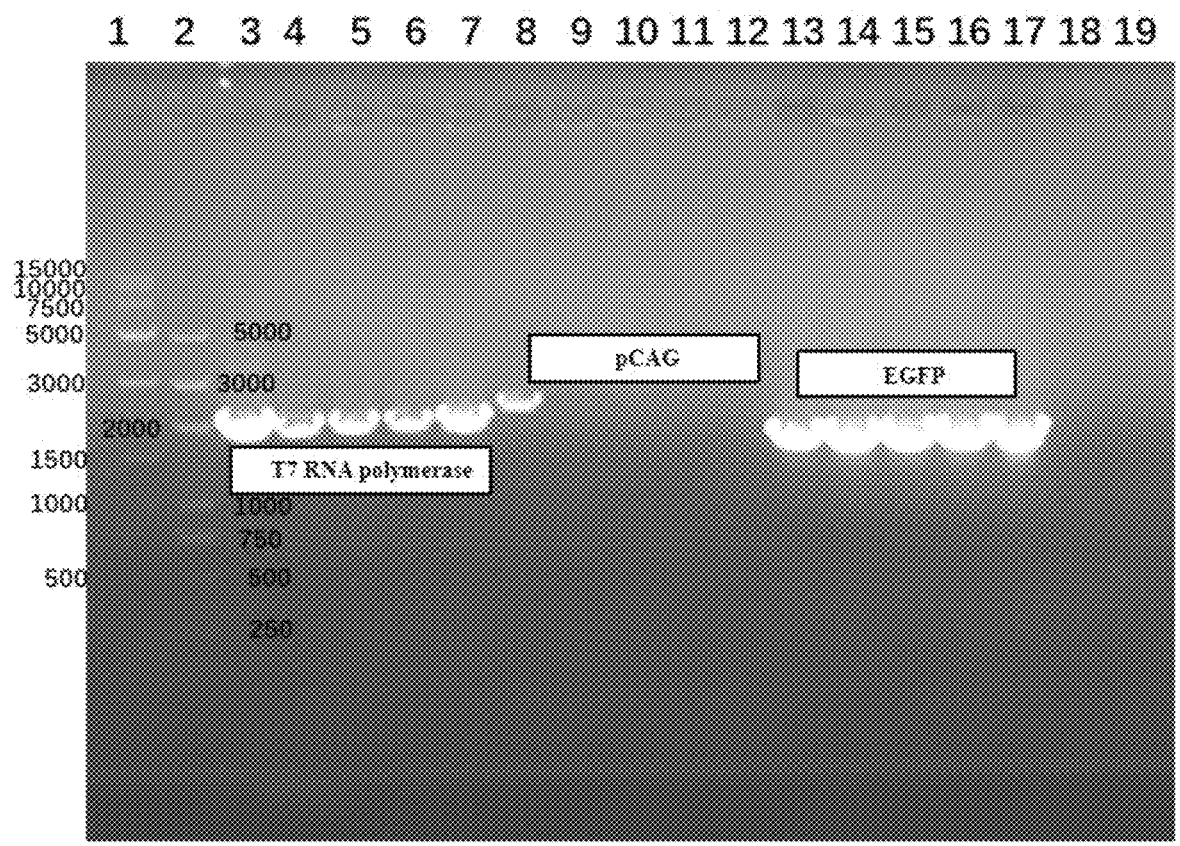
FIG. 4 shows the PCR identification of the helper plasmid pCAG-T7 RNA polymerase-EGFP, where a lane 1 is for a DNA marker DL1500, a lane 2 is for a DNA marker DL5000, lanes 3 to 7 are for amplification products of picked single colonies 1, 2, 3, 4, and 5 for a fragment T7 RNA polymerase, respectively, lanes 8 to 12 are for amplification products of picked single colonies 1, 2, 3, 4, and 5 for an enhancer fragment pCA, respectively, and lanes 13 to 17 are for amplification products of picked single colonies 1, 2, 3, 4, and 5 for an EGFP fragment, respectively.

The eukaryotic helper plasmid pCAG-T7 RNA polymerase-EGFP was transformed into DH5a competent cells, and the competent cells were coated on an LB plate including kanamycin and ampicillinum. 1 to 5 single colonies were picked, and PCR amplification was conducted with the three pairs of primers in Table 2. The electrophoresis and sequencing were conducted for identification. Results were shown in FIG. 4. It was found that a fragment amplified from a single colony 1 had a size consistent with an expected size, and a sequencing result was correct. Therefore, the single colony 1 was a positive clone carrying the eukaryotic helper plasmid pCAG-T7 RNA polymerase-EGFP.

Figures 5A, 5B:
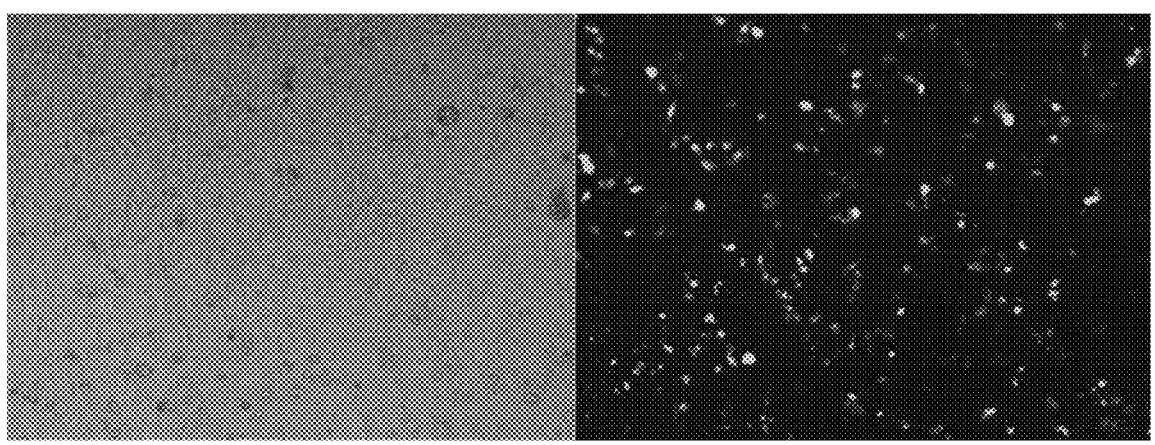
FIGS. 5A-5B show the fluorescence identification of co-transfection of a linearized backbone plasmid and helper plasmid at a mass ratio of 3:2 into veroE6, where

3. Co-Transfection in Cells and Acquisition and Passage Identification of a Recombinant Porcine Enterovirus A conventional method was used to co-transfect the linearized backbone plasmid obtained in section 1 of this example and the helper plasmid pCAG-T7 RNA polymerase-EGFP obtained in section 2 of this example into African green monkey kidney cells veroE6 with a liposome Lipofectamine™ 3000. A mass ratio of the linearized backbone plasmid to the helper plasmid was 3:2. Transfected cells were sub-cultured on veroE6 and observed under ultraviolet light with a wavelength of 488 nm. Cytopathic plaques emitting green fluorescence were picked and cultured on freshly-prepared monkey kidney cells veroE6. Then green plaques were picked several times consecutively (FIGS. 5A-5B) to produce a purified recombinant porcine enterovirus r-PEVB, which was a P0 generation.

An inappropriate liposome concentration or transfection ratio during transfection will lead to the mass dead of cells, will also greatly affect a transfection effect, and will reduce a proportion of successfully-transfected cells because a liposome itself is toxic to some extent. It was found through a large number of experiments that, when the mass ratio of the linearized backbone plasmid to the helper plasmid was 3:2, there was the highest transfection efficiency, and a fluorescence proportion after transfection reached 85% to 90% or more.

Figure 6:
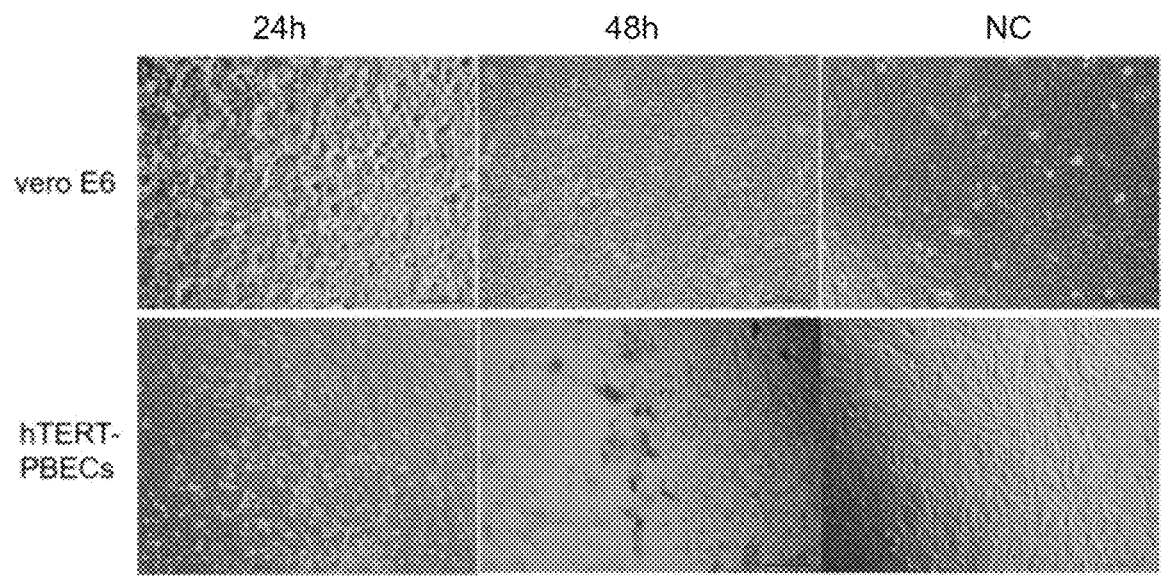
FIG. 6 shows electron microscopy images of CPEs of veroE6 and hTERT-PBECs infected with a P30-generation recombinant porcine enterovirus r-PEVB, where the first row shows CPEs of veroE6 infected with the P30-generation r-PEVB for 24 h and 48 h and a veroE6 normal cell control (NC), and the second row shows CPEs of hTERT-PBECs infected with the P30-generation r-PEVB for 24 h and 48 h and a hTERT-PBECs normal cell control (NC)

The P0 generation of the recombinant porcine enterovirus r-PEVB was passaged on immortalized porcine bronchial epithelial cells hTERT-PBECs (published in the Chinese patent application ZL201710556520.4, with an accession number CCTCC NO: C201749). A cell culture medium was prepared as follows: Australian fetal bovine serum (FBS) at a final concentration of 5% (volume percentage concentration), an antibiotic G418 at 200 μg/mL, and a complete set of epithelial cell regulatory factors in a BEGM kit (LONZA, cat.no. CC-4175) were added to a DMEM/F12 medium (Gibco). A concentration of each of the complete set of epithelial cell regulatory factors from the BEGM kit in the cell culture medium was as follows: a bovine pituitary extract (BPE): 26 μg/mL, human epithelial growth factor (hEGF): 15.5 ng/mL, human insulin: 5 μg/mL, hydrocortisone: 1.4 μM, epinephrine: 2.7 μM, iodothyronine: 9.7 nM, tretinoin: 0.3 nM, and transferrin: 10 μg/mL. The immortalized porcine bronchial epithelial cells hTERT-PBECs were cultured with the cell culture medium in a 37° C. and 5% $CO_2$ incubator. When a cell confluency reached 85% to 90%, the P0-generation recombinant porcine enterovirus r-PEVB was inoculated at $10^4 TCID_{50}$, incubated for 2 h, and washed twice with serum-free DMEM. Then the cell culture medium was replaced with a DMEM/F12 medium including 2% (volume percentage concentration) of FBS, and the culture was conducted for 72 h to 96 h. A resulting cell supernatant was collected and centrifuged at 4° C. and 1,500 rpm, and a resulting supernatant was collected as a virus solution. Then, the passage could be conducted by the same method consecutively for 30 generations or more. CPE in a passaging process was observed. CPE of a P30 generation on immortalized cells was shown in FIG. 6. RNAs of recombinant porcine enteroviruses r-pEVB of different generations were extracted, and a 5'UTR gene was determined by one-step real-time PCR with a kit HiScript III U+ One Step qRT-PCR (purchased from Vazyme, Item No. Q611) from Vazyme Biotech Co., Ltd. Primers adopted were PEVB-F and PEVB-R, and a probe adopted was PEVB-probe. A 5' terminus of the PEVB-probe was labeled with FAM, and a 3' terminus was labeled with BHQ. Specific nucleotide sequences of the primers and the probe were shown in Table 3. CT values of quantitative fluorescence PCR for P0 to P30 generations of the r-PEVB were shown in Table 4. It can be seen from Table 4 that the test results remained positive until the P30 generation, indicating that the recombinant porcine enterovirus r-PEVB can be passaged consecutively for 30 generations or more.

TABLE 3

Nucleotide sequences of the real-time PCR primers and the probe

| Primer or probe name | Primer sequence (5'-3') | Annealing temperature (° C.) |
|---|---|---|
| PEVB-F | AGGCTGACTGGACGGGGCAA (SEQ ID NO: 22) | 56 |
| PEVB-R | GCGCCTTGGGAAACGACGAG (SEQ ID NO: 23) | |
| PEVB-probe | CTACCGTTCTCGTTCTAGCTGGCCG (SEQ ID NO: 24) | 55 |

TABLE 4

CT values of real-time PCR for P0 to P30 generations (every 2 generations) of the recombinant virus r-PEVB

| Generation of r-PEVB | CT value |
|---|---|
| P0 | 18.855 |
| P2 | 18.999 |
| P4 | 19.400 |
| P6 | 22.551 |
| P8 | 23.277 |
| P10 | 24.894 |
| P12 | 24.996 |
| P14 | 25.016 |
| P16 | 25.489 |
| P18 | 25.914 |
| P20 | 26.614 |
| P22 | 27.263 |
| P24 | 29.798 |
| P26 | 31.343 |
| P28 | 32.196 |
| P30 | 33.816 |
| NC | Undetermined |

Notes:
In Table 4, NC represents a negative control, where real-time PCR is conducted with a DMEM/F12 medium instead of viral RNA.
Undetermined means that there is no detection value.

Figure 7:
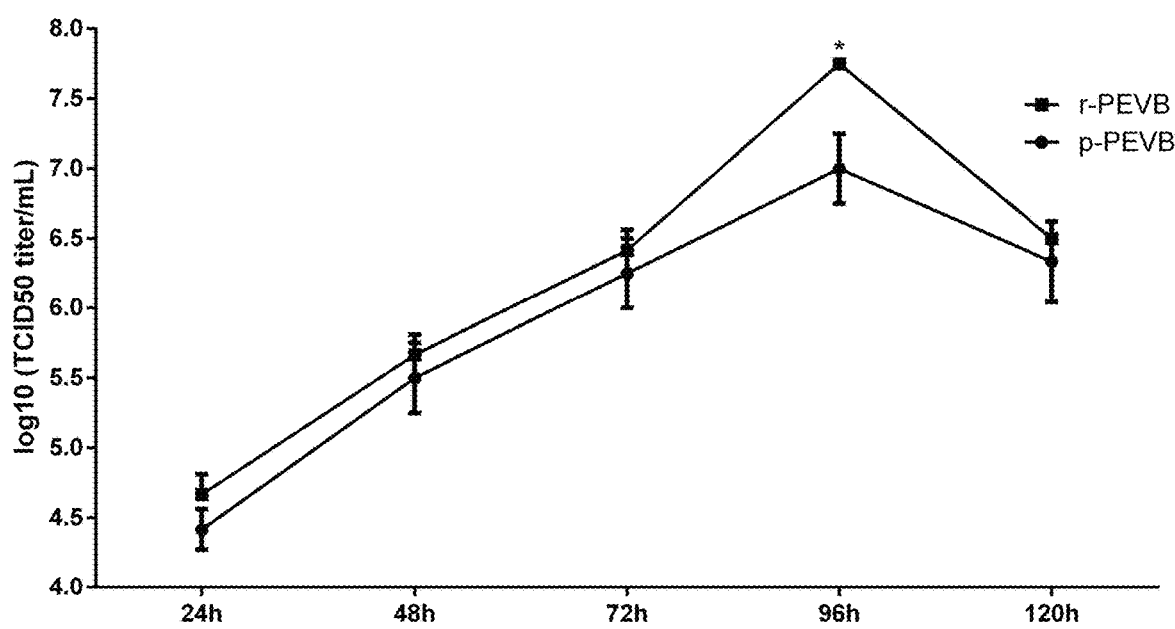
FIG. 7 shows growth curves of the recombinant porcine enterovirus r-PEVB, where p-PEVB represents a parental strain PEV-B-KOR.

4. Identification and Biological Characteristic Study for the Recombinant Porcine Enterovirus r-PEVB 4.1 Determination of $TCID_{50}$ of the Recombinant Virus on Porcine Bronchial Epithelial Cells hTERT-PBECs Growth curves of a porcine enterovirus parental strain (a PEVB strain PEV-B-KOR) and the recombinant porcine enterovirus r-PEVB were determined on porcine bronchial epithelial cells hTERT-PBECs. A specific method was as follows: hTERT-PBECs were infected with each of the recombinant porcine enterovirus r-PEVB (P25 generation) and the parental strain PEV-B-KOR strain (P5 generation) at $10^3 TCID_{50}$, incubated for 2 h, and then cultured with a DMEM/F12 medium including 2% (volume percentage concentration) of FBS instead in a 37° C. and 5% $CO_2$ incubator. At 24 h, 48 h, 72 h, 96 h, and 120 h after the inoculation, virus samples were collected and subjected to three freeze-thaw cycles. $TCID_{50}$ of a virus sample at each time point was determined. A one-step growth curve of the recombinant porcine enterovirus r-PEVB was plotted according to viral titers. A difference in growth kinetics between the recombinant porcine enterovirus and the parental strain as a control was determined. According to results (FIG. 7): The recombinant porcine enterovirus r-PEVB exhibited a higher growth titer than the parental strain overall. A $TCID_{50}$ titer of the recombinant porcine enterovirus r-PEVB was $10^{7.75} TCID_{50}$/mL at 96 h after infection, which was 1 $TCID_{50}$ higher than a titer of the strain PEV-B-KOR and 0.75 $TCID_{50}$ higher than a titer of a wild-type parental strain cultured on veroE6, and remained stable. In addition, the recombinant porcine enterovirus r-PEVB exhibited a significantly-higher infection efficiency and titer on immortalized porcine bronchial epithelial cells than on African green monkey kidney cells veroE6. These results indicate that the constructed recombinant porcine enterovirus has a prominent replication ability.

4.2 Identification of the Recombinant Porcine Enterovirus r-PEVB

Figure 8:
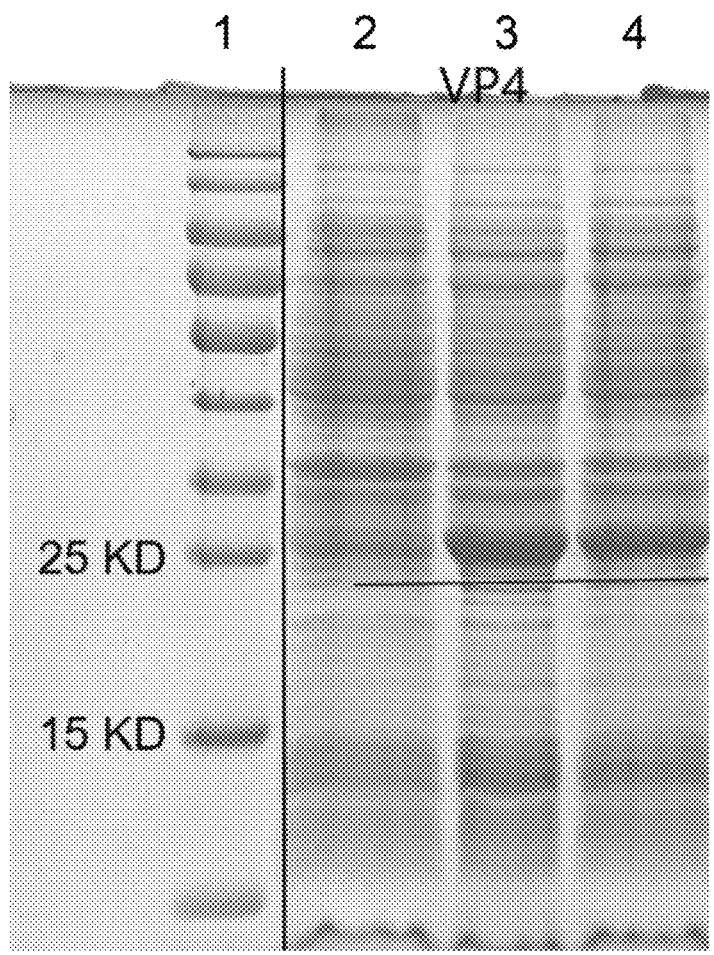
FIG. 8 is a sodium dodecyl sulfate-polyacrylamide gel electrophoresis (SDS-PAGE) pattern of prokaryotic mass expression of a recombinant VP4 protein, where a lane 1 is for a protein Marker, a lane 2 is for a VP4-32a lysate before induction, and lanes 3 and 4 both are for a precipitate of the VP4-32a lysate after induction.
Figure 9:
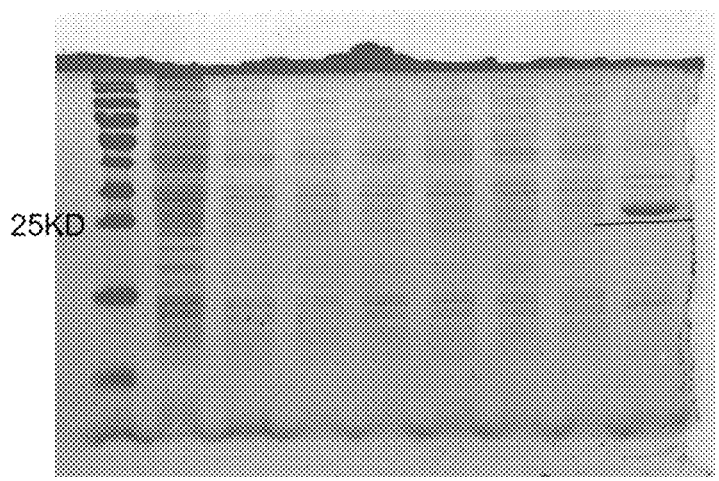
FIG. 9 shows the mass purification of the recombinant VP4 protein after inclusion body extraction, where lanes from left to right are sequentially for the following: a protein Marker, a precipitate produced after ultrasonic lysis of induced bacteria, a supernatant produced after ultrasonic lysis of induced bacteria, an eluate collected during elution of a Ni column with 20 mM imidazole, an eluate collected during elution of a Ni column with 50 mM imidazole, an eluate collected during elution of a Ni column with 100 mM imidazole, an eluate collected during elution of a Ni column with 250 mM imidazole, an eluate collected during elution of a Ni column with 300 mM imidazole, and a VP4 protein resulting from purification and renaturation of an inclusion body produced after elution with 500 mM imidazole.

A VP4 protein gene of PEVB (a sequence was shown in SEQ ID NO: 1) was inserted into a protein expression vector pET-32a, and then a resulting protein expression vector was introduced into an *E. coli* host to produce recombinant bacteria VP4-32a. The expression of a recombinant VP4 protein (carrying his-tag) was induced with isopropylthio-β-galactoside (IPTG). A precipitate resulting from lysis of recombinant bacteria VP4-32a included a large amount of a target protein (FIG. 8), indicating that the target protein was mainly expressed in the form of an inclusion body. A high-affinity Ni column (purchased from GenScript, Item No.: L00666) was adopted. According to specific steps of instructions, recombinant bacteria VP4-32a produced after the induced expression were subjected to lysis, and a resulting precipitate was loaded on the Ni column. Then elution was conducted with 20 mM imidazole, 50 mM imidazole, 100 mM imidazole, 250 mM imidazole, 300 mM imidazole, and 500 mM imidazole solutions successively, and an eluate of an imidazole solution at each concentration was collected. The recombinant VP4 protein was found in an eluate of 500 mM imidazole. The recombinant VP4 protein was renatured with a renaturation solution according to a conventional method. The renaturation solution was prepared as follows: L-Arg HCl at a final concentration of 400 mM, EDTA at 2 mM, glutathione (GSH) at 5 mM, glutathione disulfide (GSSG) at 1 mM, and phenylmethylsulfonyl fluoride (PMSF) at 0.5 mM were added to a Tris buffer with a concentration of 100 mM and a pH of 8.0. It can be seen from FIG. 9 that the renatured recombinant VP4 protein had a specific band at 25 KD, and a large number of impurity proteins were removed.

The renatured recombinant VP4 protein as an immunogen was inoculated into New Zealand white rabbits to prepare a rabbit-derived anti-VP4 protein polyclonal antibody. According to ELISA antibody detection (the renatured recombinant VP4 protein was coated at 3 µg/well), the renatured recombinant VP4 protein had an ELISA antibody titer of 100,000 or more. The rabbit-derived anti-VP4 protein polyclonal antibody could be used subsequently for the IFA and WB identification of r-PEVB (P25).

4.2.1 IFA Identification

Figure 10A:
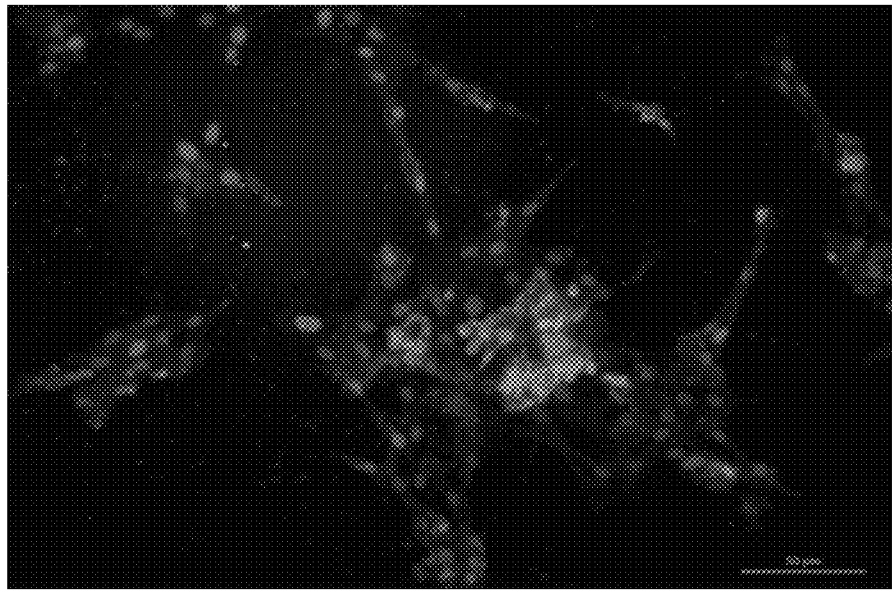
FIGS. 10A-10C show the indirect immunofluorescence assay (IFA) verification for the recombinant porcine enterovirus r-PEVB with a rabbit-derived anti-VP4 protein polyclonal antibody as a primary antibody, where
Figure 10B:
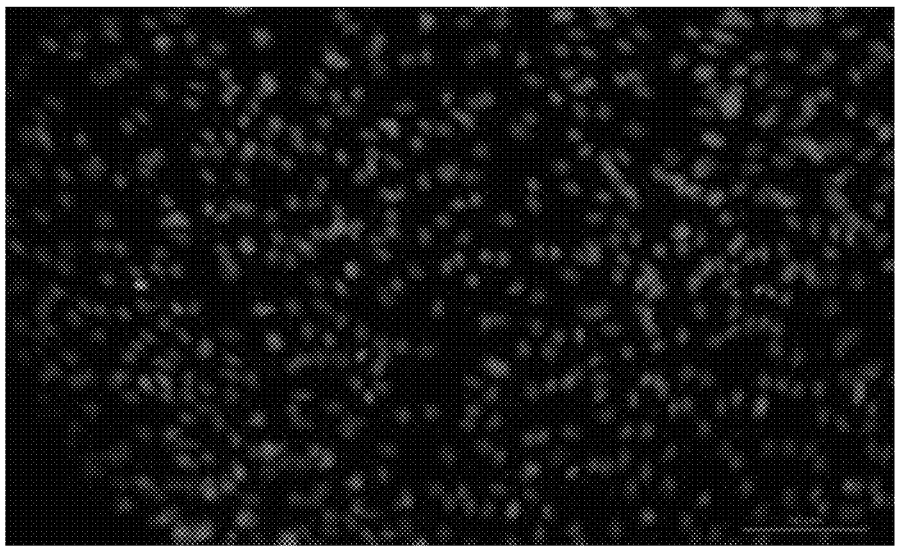
Figure 10C:
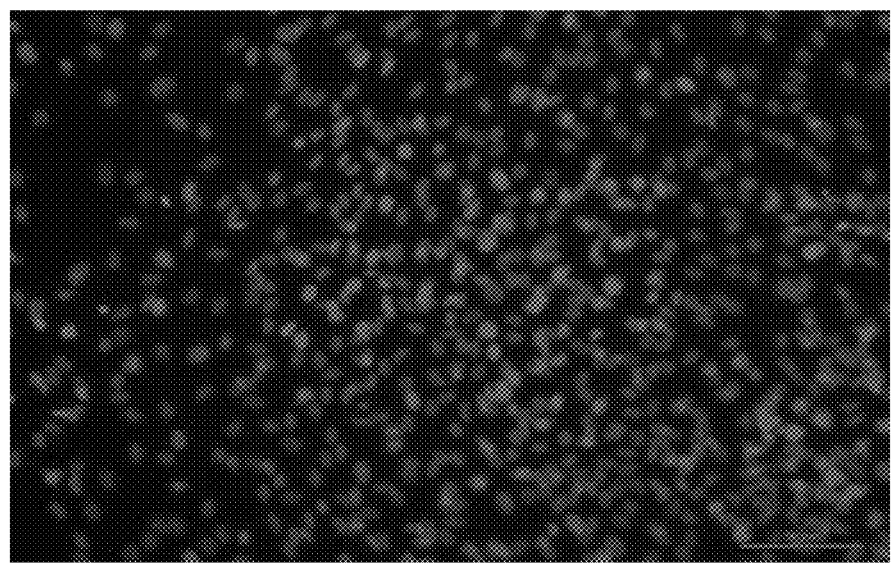

The recombinant porcine enterovirus r-PEVB was cultured with porcine bronchial epithelial cells hTERT-PBECs for 96 h, fixed with paraformaldehyde, then washed with phosphate buffered saline (PBS) 3 times, permeabilized with a 0.2% Triton X-100 aqueous solution at room temperature for 5 min, washed with PBS 3 times, blocked with a 3% BSA aqueous solution at room temperature for 1 h, washed with PBS 3 times, incubated with the rabbit-derived anti-VP4 protein polyclonal antibody as a primary antibody overnight at 4° C., washed with PBS 3 times, incubated with Alexa Fluor 555-labeled donkey anti-rabbit IgG (H+L) (purchased from Beyotime, Item No.: A0453) at 37° C. for 1 h in the dark, washed with PBS 3 times, and observed under a fluorescence microscope. Porcine bronchial epithelial cells hTERT-PBECs not infected with the recombinant porcine enterovirus r-PEVB were adopted as NC. Porcine bronchial epithelial cells hTERT-PBECs that were not infected with the recombinant porcine enterovirus r-PEVB and incubated with PBS instead of the rabbit-derived anti-VP4 protein polyclonal antibody were adopted as a blank control. It can be seen from FIGS. 10A-10C that a recombinant porcine enterovirus r-PEVB culture had red specific fluorescence, indicating that the recombinant virus r-PEVB was successfully constructed.

4.2.2 WB Identification

Figure 11A:
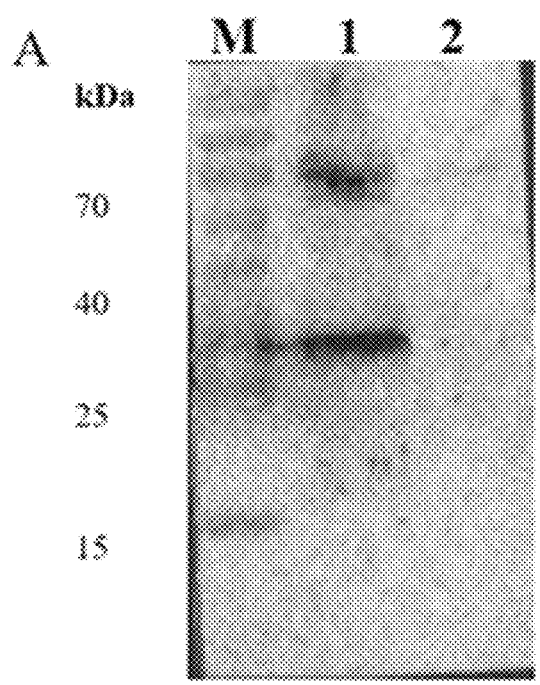
FIGS. 11A-11B show the western blotting (WB) verification for the recombinant porcine enterovirus r-PEVB using a rabbit-derived anti-VP4 protein polyclonal antibody and His antibody, where in FIG. 11A, a lane M is for a protein Marker, and lanes 2 and 3 show WB verification results of a protein produced by hTERT-PBECs infected with the recombinant virus r-PEVB and a protein produced by hTERT-PBECs not infected with the recombinant virus r-PEVB using the rabbit-derived anti-VP4 protein polyclonal antibody, respectively; and in FIG. 11B, a lane M is for a protein Marker, and a lane 1 shows a WB verification result of a protein produced by hTERT-PBECs infected with the recombinant virus r-PEVB using the rabbit-derived His antibody.
Figure 11B:
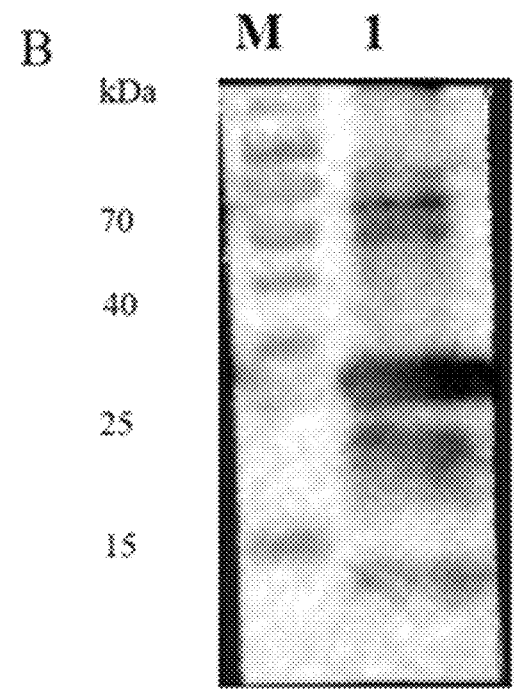

Porcine bronchial epithelial cells hTERT-PBECs (normal control), porcine bronchial epithelial cells hTERT-PBECs infected with the recombinant porcine enterovirus r-PEVB, and porcine bronchial epithelial cells hTERT-PBECs infected with the parental strain (the PEVB strain PEV-B-KOR) each were collected and subjected to total protein extraction with an RIPA protein lysis buffer (Item No. P0013B) of Beyotime. Each total protein was subjected to SDS-PAGE and then transferred to a PVDF membrane. The membrane was taken out, washed with PBST 3 times, blocked with a 5% skimmed milk solution at 37° C. for 2 h, washed with PBST 3 times, incubated with the rabbit-derived anti-VP4 protein polyclonal antibody (prepared in section 4.2 of this example) overnight at 4° C., washed with PBST 3 times, incubated with horseradish peroxidase-labeled goat anti-rabbit IgG (H+L) (purchased from Beyotime, Item No. A0208) at room temperature for 1 h, washed with PBST 3 times, and subjected to electrochemiluminescence (ECL). In addition, the hTERT-PBECs infected with the recombinant porcine enterovirus r-PEVB were subjected to WB verification with a his antibody by the same method as the WB verification with the rabbit-derived anti-VP4 protein polyclonal antibody, except that the his antibody (purchased from BOSTER, Item No.: M30975-) was used instead of the rabbit-derived anti-VP4 protein polyclonal antibody. Specific results were shown in FIGS. 11A-11B. The results showed that a protein produced by the hTERT-PBECs infected with the recombinant porcine enterovirus r-PEVB could react specifically with the rabbit-derived anti-VP4 protein polyclonal antibody and the His antibody, and specific bands appeared in lanes, indicating that the recombinant virus r-PEVB of PEVB was successfully constructed.

Example 2 Application of a Viral Vector for Both Respiratory and Digestive Tracts of Pigs 1. Research on Related Characteristics of the Recombinant Porcine Enterovirus r-PEVB as a Viral Vector A gene sequence (SEQ ID NO: 2) for a T cell epitope of ASFV was inserted between a VP4 gene and a 5'UTR gene of the recombinant porcine enterovirus r-pEVB to produce a recombinant expression plasmid A-T-r-PEVB. An amino acid sequence for the T cell epitope of ASFV was shown in SEQ ID NO: 3. The gene fragment for the T cell epitope of ASFV was synthesized by GenScript. A specific method for constructing the recombinant expression plasmid A-T-r-PEVB was as follows: The recombinant plasmid pUC57-PEVB constructed in Example 1 was cleaved with EcoRI and HindIII, and then ligated with the synthesized gene fragment for the T cell epitope of ASFV by a conventional method with a T4 DNA ligase to produce the recombinant expression plasmid A-T-r-PEVB.

A gene (SEQ ID NO: 4) for a B cell epitope of a major protective adhesion factor antigen P97R1 of Mhp was inserted between a VP4 gene and a 5'UTR gene of the recombinant porcine enterovirus r-pEVB to produce a recombinant expression plasmid M-r-PEVB. An amino acid sequence for the B cell epitope of the major protective adhesion factor antigen P97R1 of Mhp was shown in SEQ ID NO: 5. A specific method for constructing the recombinant expression plasmid M-r-PEVB was as follows: The recombinant plasmid pUC57-PEVB constructed in Example 1 was cleaved with EcoR1 and HindIII, and then ligated with the synthesized gene fragment for the B cell epitope of P97R1 by a conventional method with a T4 DNA ligase to produce the recombinant expression plasmid M-r-PEVB.

A gene fragment with a sequence shown in SEQ ID NO: 6 that included the T cell epitope of ASFV and the B cell epitope of P97R1 of Mhp was inserted between a VP4 gene and a 5'UTR gene of the recombinant porcine enterovirus r-pEVB to produce a recombinant expression plasmid A-M-r-PEVB. An amino acid sequence including the T cell epitope of ASFV and the B cell epitope of P97R1 of Mhp was shown in SEQ ID NO: 7. A specific method for constructing the recombinant expression plasmid A-M-r-PEVB was as follows: The recombinant plasmid pUC57-PEVB constructed in Example 1 was cleaved with EcoRI and HindIII, and then ligated with the synthesized gene fragment with the sequence shown in SEQ ID NO: 6 by a conventional method with a T4 ligase to produce the recombinant expression plasmid A-M-r-PEVB.

The recombinant expression plasmids each were cleaved with EcoRI and then identified by electrophoresis. Results were shown in FIGS. 12A-12C, which were consistent with the expected results. The recombinant expression plasmids A-T-r-PEVB, M-r-PEVB, and A-M-r-PEVB each were cleaved with a restriction endonuclease Pac I to produce linearized fragments L-A-T-r-PEVB, L-M-r-PEVB, and L-A-M-r-PEVB, respectively. A liposome lipo3000 was used to co-transfect each linearized fragment with the helper plasmid pCAG-T7-polymerase-EGFP at a mass ratio of 2:1 into monkey kidney cells veroE6. A transfection PC group (only the helper plasmid was transfected into monkey kidney cells veroE6 with a liposome lipo3000) and an NC group (monkey kidney cells veroE6 were co-transfected with ultrapure water and a liposome lipo3000) were also set. Transfected cells were sub-cultured and observed under ultraviolet light with a wavelength of 488 nm. Cytopathic plaques emitting green fluorescence were picked and cultured on freshly-prepared monkey kidney cells veroE6. Then green plaques were picked several times consecutively (FIG. 13) to produce purified recombinant viruses A-T-r-PEVB, M-r-PEVB, and A-M-r-PEVB, which were denoted as P0 generations.

The recombinant viruses A-T-r-PEVB, M-r-PEVB, and A-M-r-PEVB could be passaged continuously on hTERT-PBECs, and could be stably passaged for 25 generations or more. During a passaging process, CPE was observed. CPE of a P14 generation on immortalized hTERT-PBECs was shown in FIG. 14. Different generations of each recombinant virus were collected and subjected to RNA extraction, and one-step real-time PCR detection was conducted with HiScript III U+ One Step qRT-PCR (purchased from Vazyme, Item No.: Q611) according to the method in section 3 of Example 1. P0 to P30 generations of each recombinant virus were detected by quantitative fluorescence PCR every 5 generations, and corresponding CT values were shown in Table 5. The P25 generation or before was stable, and a viral titer could reach $10^{7.25}$ TCID$_{50}$/mL.

TABLE 5

CT values of real-time PCR for P0 to P30 generations (measured every 5 generations) of each recombinant virus

| Generation of the recombinant virus A-T-r-PEVB | CT value | Generation of the recombinant virus M-r-PEVB | CT value | Generation of the recombinant virus A-M-r-PEVB | CT value |
| --- | --- | --- | --- | --- | --- |
| P0 | 18.400 | P0 | 18.158 | P0 | 18.499 |
| P5 | 23.277 | P5 | 27.551 | P5 | 24.894 |
| P10 | 26.016 | P10 | 23.996 | P10 | 28.489 |
| P15 | 28.614 | P15 | 27.914 | P15 | 25.263 |
| P20 | 30.343 | P20 | 30.174 | P20 | 29.798 |
| P25 | 31.770 | P25 | 31.816 | P25 | 30.196 |
| P30 | 35.500 | P30 | 34.794 | P30 | 35.137 |
| NC | Undetermined | | | | |

Note:
NC in Table 5 represents a negative medium control.

A plurality of sites had also be selected by the applicants for inserting the cell epitope genes of the above three antigens. It was found that there was a very low transfection efficiency of less than 10%, such as inserting between a 2A gene and a VP1 gene.

2. Identification of Each Recombinant Virus hTERT-PBECs were cultured according to the method in section 3 of Example 1. The recombinant viruses A-T-r-PEVB, M-r-PEVB, and A-M-r-PEVB of a P25 generation each were inoculated for proliferation, and cultured for 72 h to 96 h. Three freeze-thaw cycles were conducted, and centrifugation was conducted at 10,000 rpm and 4° C. for 10 min. IFA and WB were conducted for identification. Uninfected hTERT-PBECs were adopted as NC. For the PEVB VP4 protein, with a rabbit-derived anti-VP4 protein polyclonal antibody as a primary antibody and Alexa Fluor 555-labeled donkey anti-rabbit IgG (H+L) (purchased from Beyotime, Item No. A0453) as a secondary antibody, the recombinant viruses A-T-r-PEVB, M-r-PEVB, and A-M-r-PEVB each were identified by IFA and WB. For the recombinant virus M-r-PEVB, with an Mhp P97R1 antibody (published in Xie Xing et al., 2022, Construction of a telomerase-immortalized porcine tracheal epithelial cell model for swine-origin *mycoplasma* infection, Journal of Integrative Agriculture 2022, 21 (2): 504-520) as a primary antibody and Alexa Fluor 555-labeled donkey anti-mouse IgG (H+L) (purchased from Beyotime, Item No. A0460) as a secondary antibody, IFA and WB were conducted. For the recombinant virus A-T-r-PEVB, with an ASFV-positive serum antibody as a primary antibody and an FITC-labeled goat anti-pig fluorescent secondary antibody (purchased from Beijing Biodragon, Item No. BD9448) as a secondary antibody, IFA and WB were conducted. For A-M-r-PEVB, with an ASFV-positive serum antibody as a primary antibody and an FITC-labeled goat anti-pig fluorescent secondary antibody (purchased from Beijing Biodragon, Item No. BD9448) as a secondary antibody, IFA and WB were conducted, and IFA and WB were also conducted with an Mhp P97R1 antibody. Porcine bronchial epithelial cells hTERT-PBECs not infected with the recombinant porcine enterovirus r-PEVB were adopted as NC for both IFA and WB identification.

Figure 15:
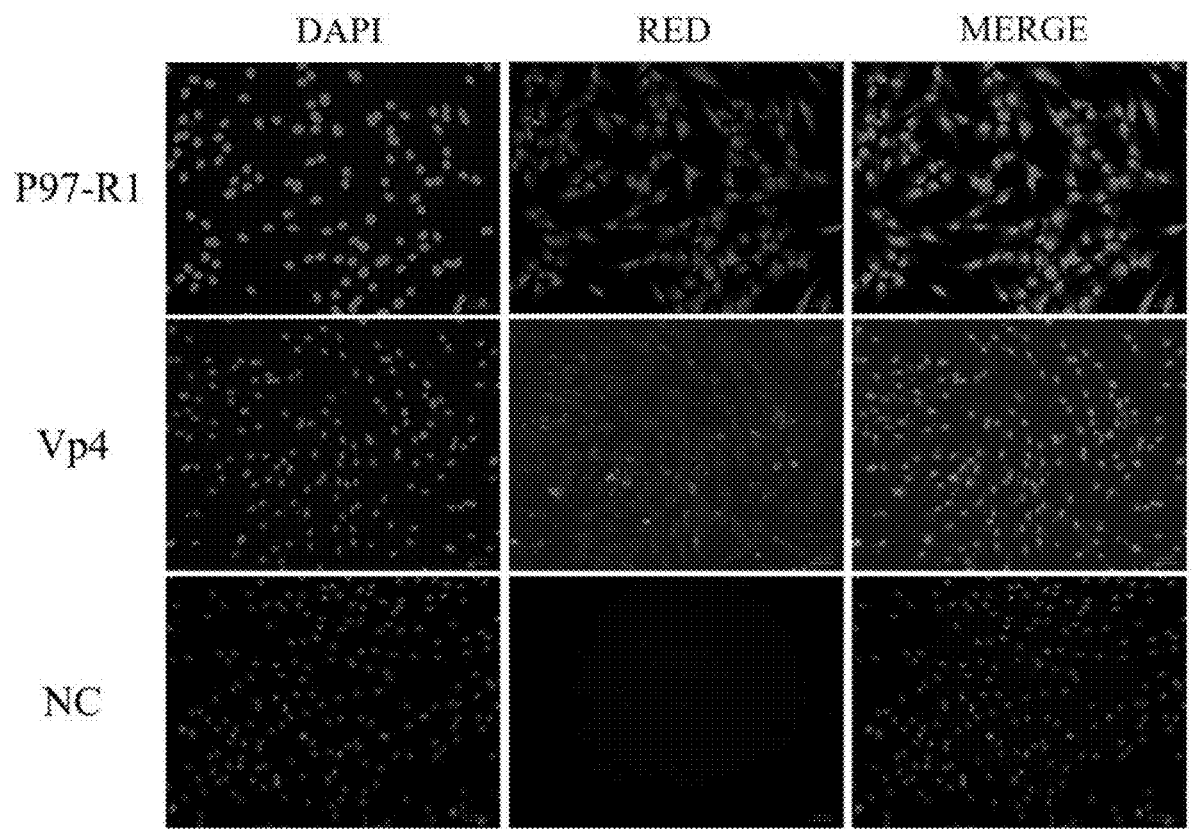
Figure 16:
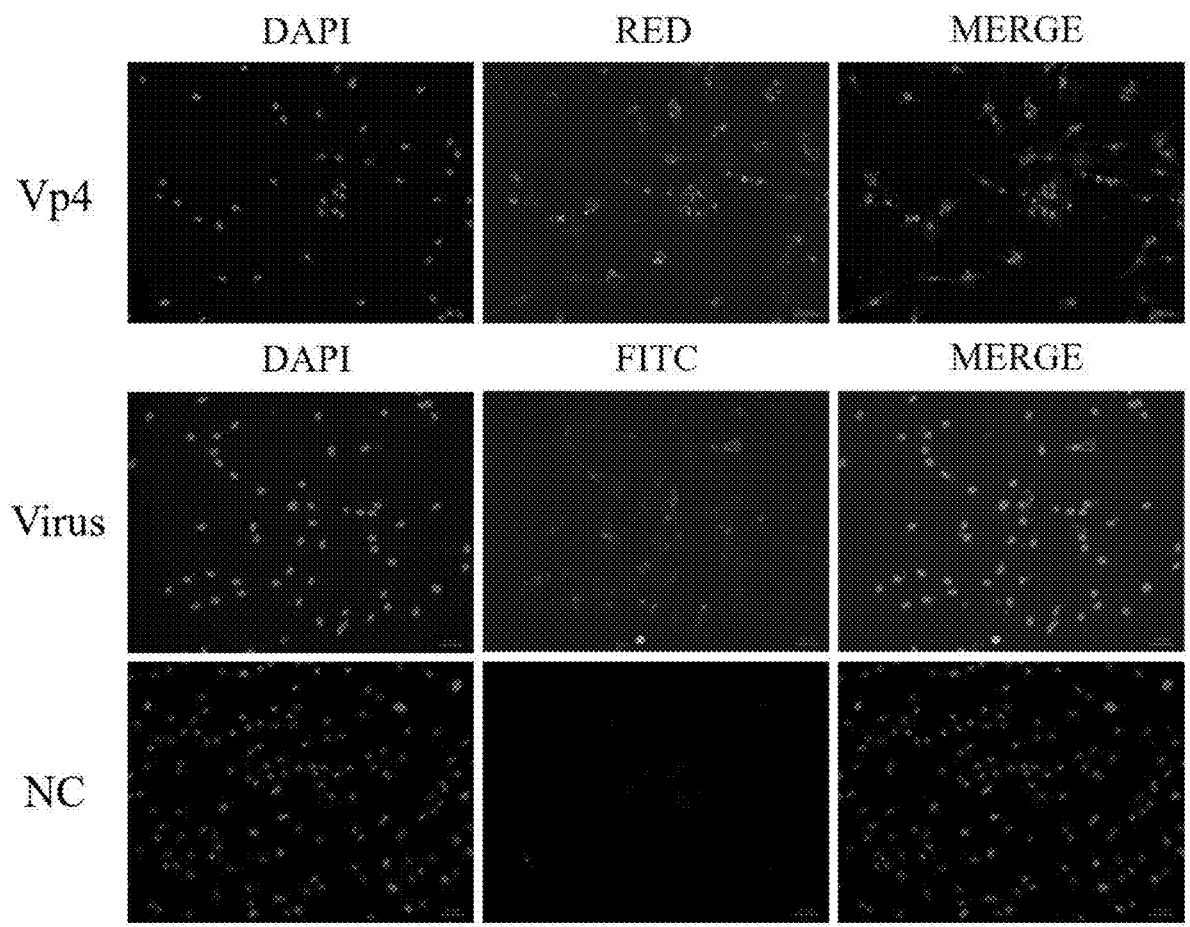
Figure 17:
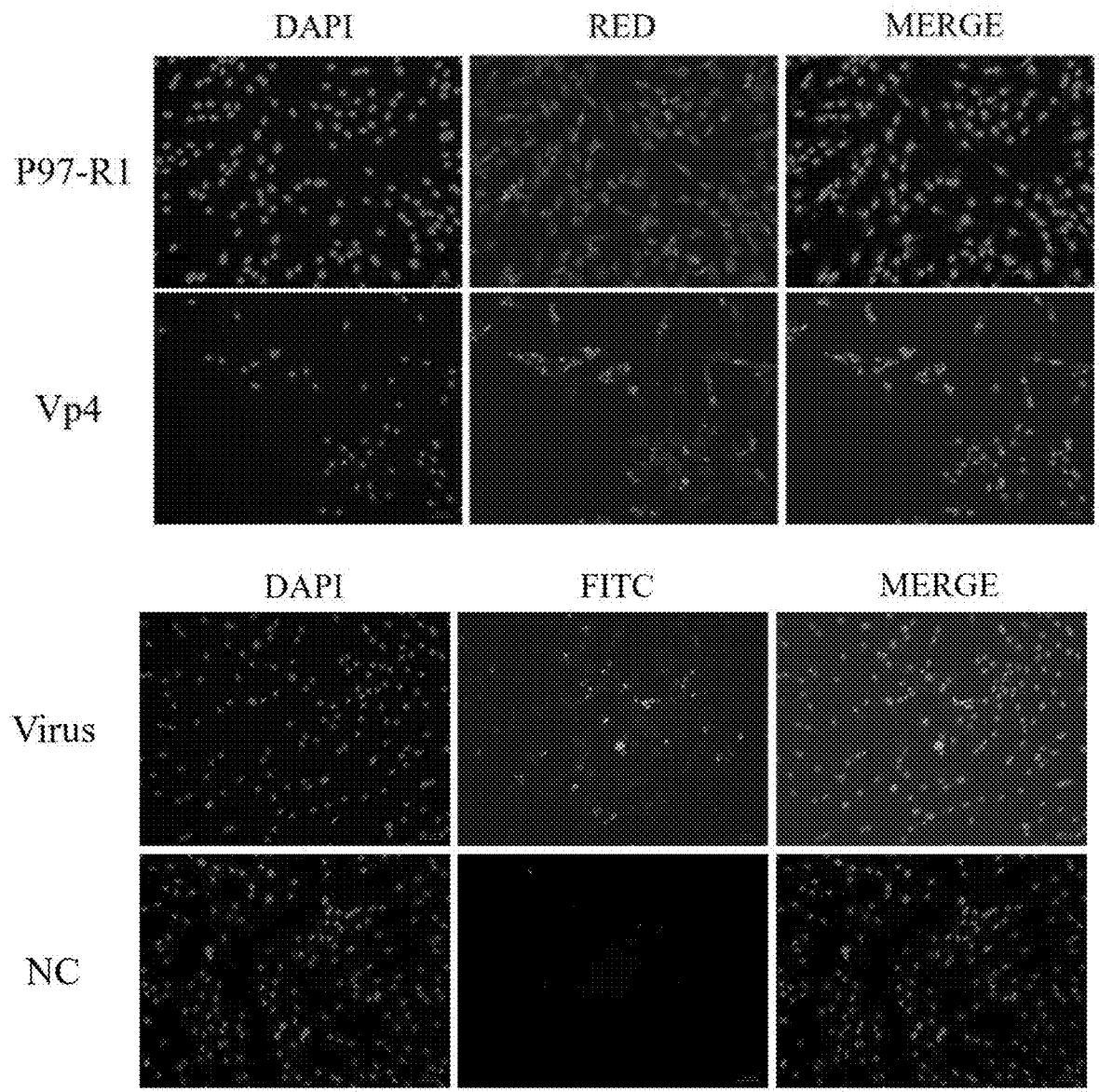

Results of IFA (FIG. 15 to FIG. 17) showed that the recombinant virus A-T-r-PEVB carrying the T cell epitope of ASFV, the recombinant virus M-r-PEVB carrying the B cell epitope of Mhp P97R1, and the recombinant virus A-M-r-PEVB carrying the T cell epitope of ASFV and the B cell epitope of Mhp P97R1 were successfully constructed, and presented specific green, red, and red fluorescence respectively compared with NC (porcine bronchial epithelial cells hTERT-PBECs not infected with the recombinant porcine enterovirus r-PEVB). When the recombinant porcine enterovirus PEVB was identified with IFA, a rabbit-derived VP4 protein polyclonal antibody was adopted as a primary antibody and Alexa Fluor 555-labeled donkey anti-rabbit IgG (H+L) was adopted as a secondary antibody. The successfully-constructed recombinant porcine enterovirus PEVB could emit red fluorescence through indirect immunofluorescence detection of VP4 protein. When the African swine fever virus epitope was identified with IFA, an African swine fever virus-positive serum antibody was adopted as a primary antibody and FITC-labeled sheep anti-pig antibody was adopted as a secondary antibody. If positive, specific green fluorescence could be observed under a microscope during IFA. When the epitope of P97R1 was identified with IFA, an anti-P97R1 protein monoclonal antibody was adopted as a primary antibody and Alexa Fluor 555-labeled donkey anti-mouse IgG (H+L) was adopted as a secondary antibody. If positive, red fluorescence would be emitted.

Figure 18:
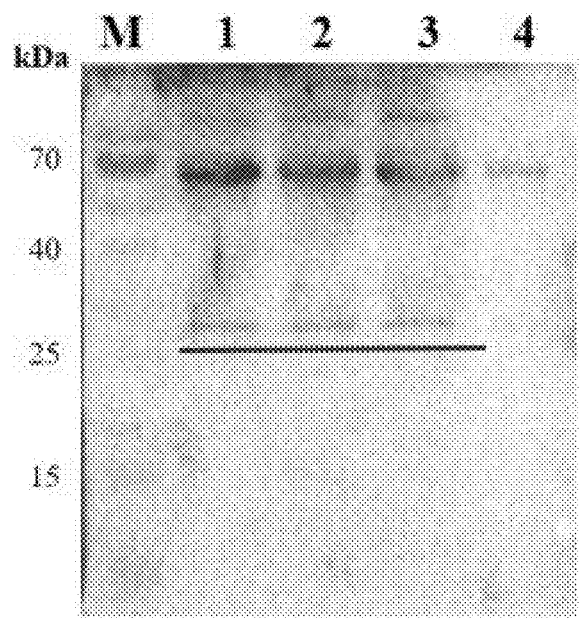
Figure 19:
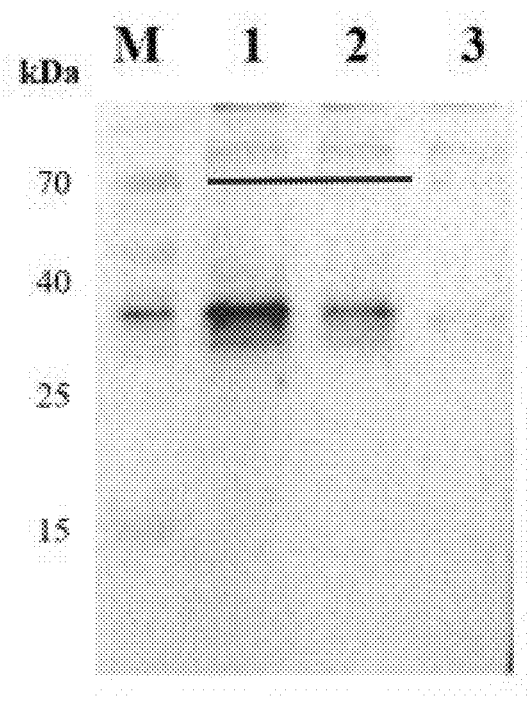
Figures 20, 21A, 21B, 22A:
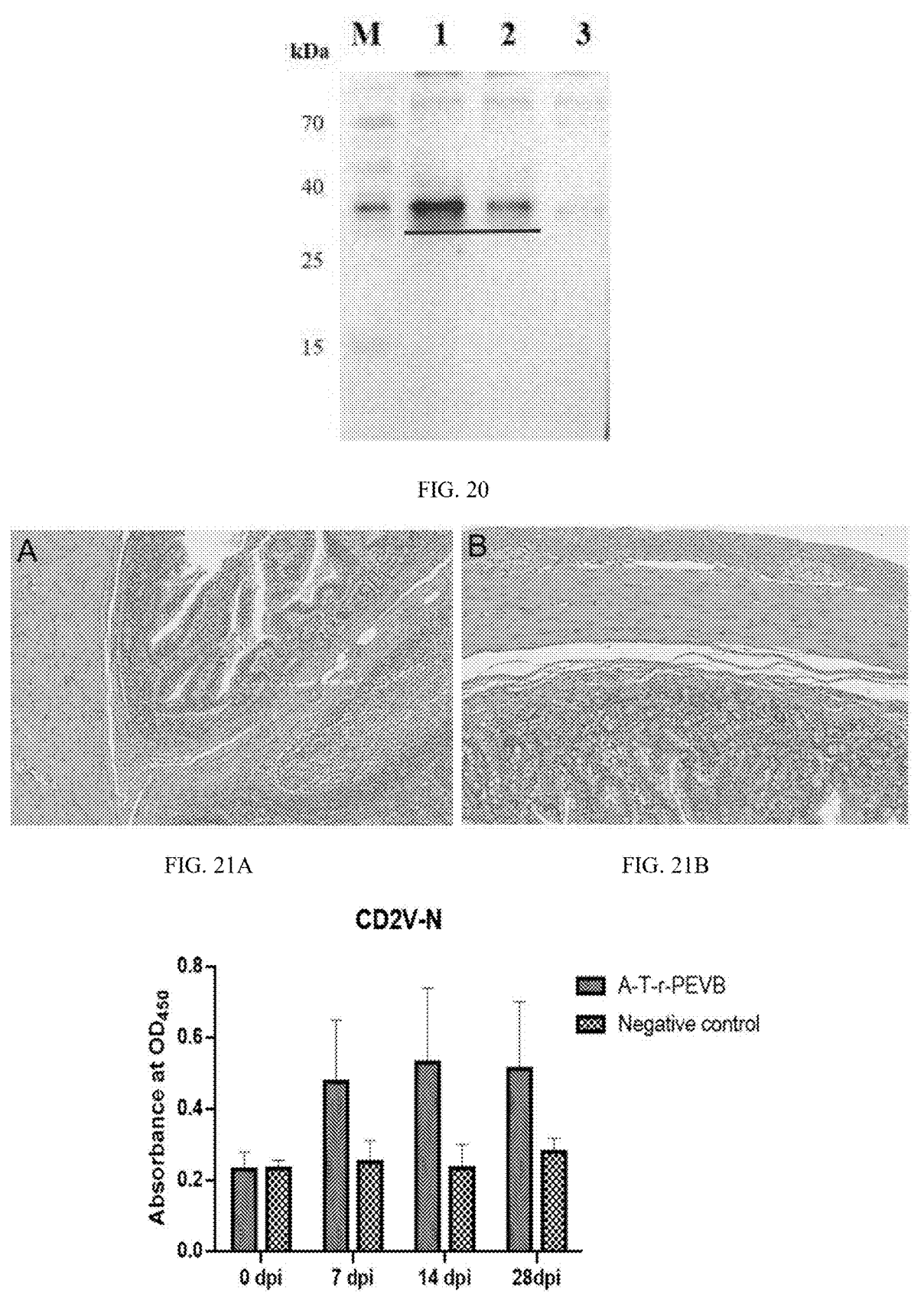
Figure 22B:
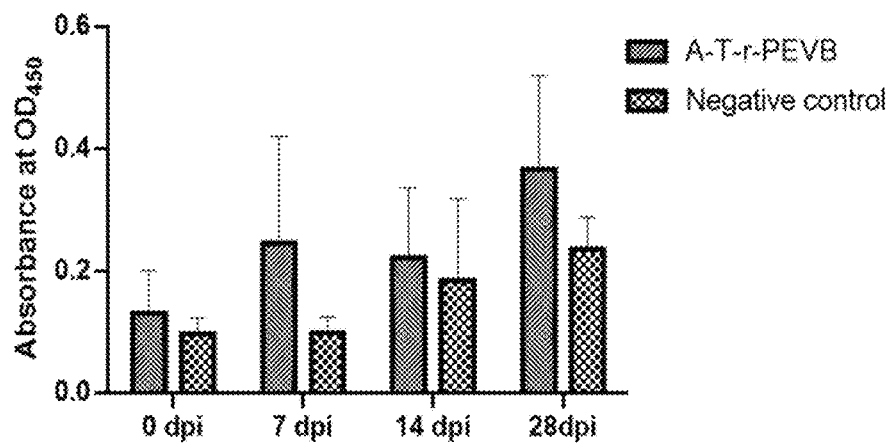
Figure 22C:
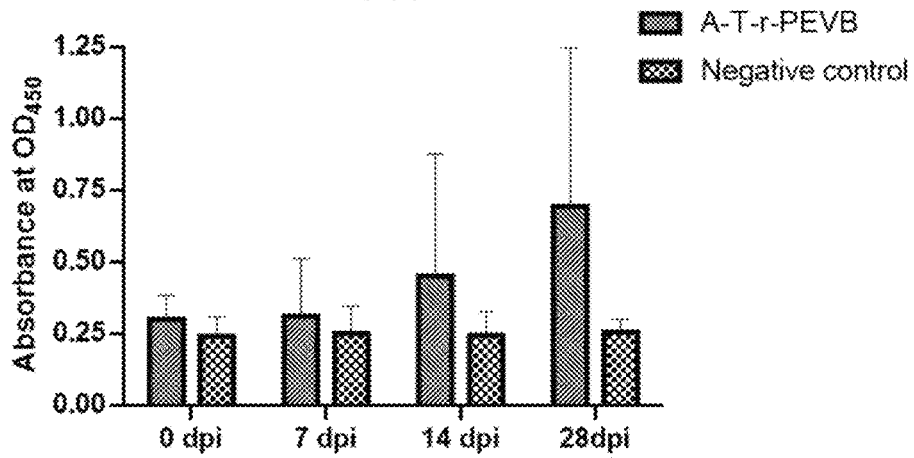
Figure 22D:
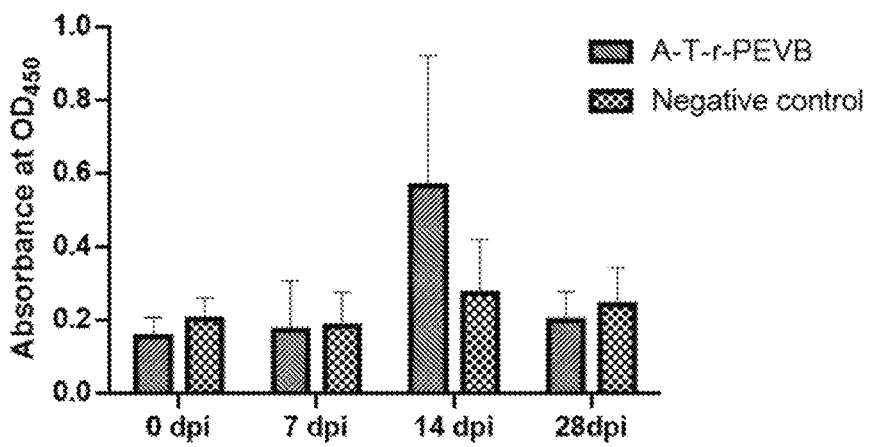
Figure 22E:
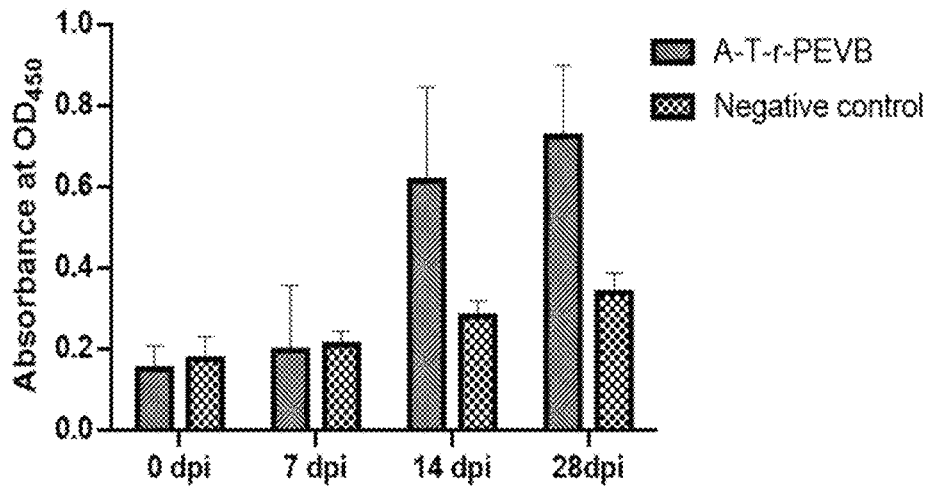
Figure 22F:
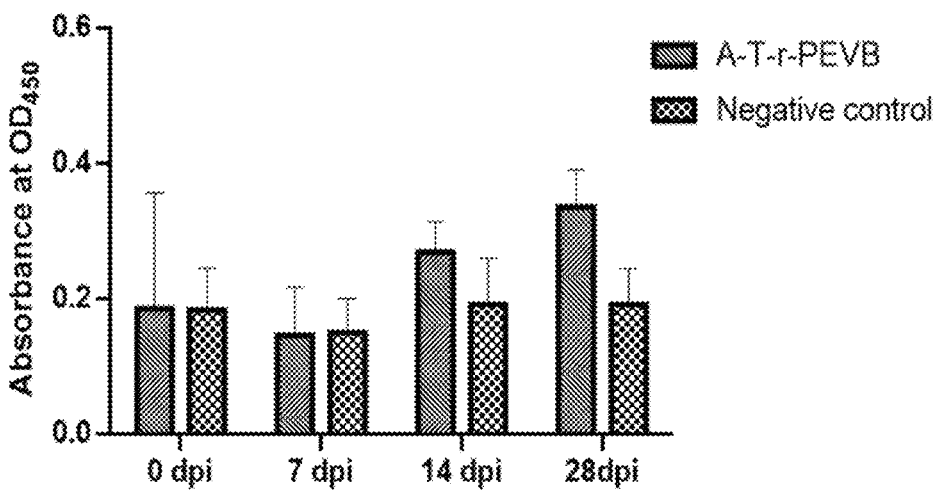

As shown in FIG. 18 to FIG. 20, compared with NC (hTERT-PBECs not infected with a virus), there were obvious specific bands for each recombinant virus. According to WB identification results of the recombinant viruses A-M- r-PEVB, A-T-r-PEVB, and M-r-PEVB against the rabbit-derived anti-VP4 protein polyclonal antibody in FIG. 18, a specific band appeared at 25 KD, indicating that the above viruses were recombinant enteroviruses. According to WB identification results of the recombinant viruses A-M-r-PEVB and M-r-PEVB against the Mhp P97R1 monoclonal antibody in FIG. 19, a specific band appeared at 29 KD, indicating that the Mhp P97R1 epitope was successfully inserted in the recombinant viruses. According to WB identification results of the recombinant viruses A-M-r-PEVB and A-T-r-PEVB against the ASFV-positive serum antibody in FIG. 20, two specific bands appeared at 70 KD and 55 KD, respectively, indicating that the African swine fever virus epitope was successfully inserted. No bands or only a few weak and shallow bands appeared for the NC, indicating that each recombinant virus was successfully constructed, and a recombinant viral vector-expressing strain r-PEVB with an ASFV and/or Mhp antigen inserted was successfully acquired.

3. Immunogenicity (Mhp and ASFV) of Pigs Immunized with Each Recombinant Virus and Protective Efficacy Evaluation (Mhp)

The feasibility of using the recombinant virus r-PEVB as a viral vector of a vaccine for both respiratory and digestive tracts of pigs was comprehensively evaluated.

A preparation method of each recombinant virus was as follows: The recombinant virus r-PEVB that was passaged on hTERT-PBECs to the 14th generation (P14) and cryopreserved at −70° C. was subjected to expansion culture on hTERT-PBECs for 96 h until obvious CPE was observed. Three freeze-thaw cycles were conducted, centrifugation was conducted, and a resulting supernatant was collected as the recombinant virus r-PEVB. Preparation methods of the recombinant viruses A-T-r-PEVB and M-r-PEVB were the same as the preparation method of the recombinant virus r-PEVB. Thus, all recombinant viruses for immunization were of the 15th generation.

(1) Evaluation of Safety of the Recombinant Virus r-PEVB and a Parental Strain PEV-B-KOR in Pigs The recombinant virus r-PEVB of 106.5 $TCID_{50}$/mL and the strain PEV-B-KOR of 106.5 $TCID_{50}$/mL each were intramuscularly injected into 10-day-old SPF pigs at a dose of 2 mL/pig, and clinical symptoms were observed within 14 d. The necropsy was conducted 14 d later. The results showed that, like the parental strain, the recombinant virus r-PEVB did not cause any clinical symptoms or diarrhea after being intramuscularly injected into pigs. The intestinal pathological sections (FIGS. 21A-21B) showed that everything was normal, indicating that the recombinant virus r-PEVB is non-pathogenic and is safe as a live vaccine vector.

(2) Immunogenicity of the Recombinant Virus a-T-r-PEVB Against ASFV after Immunization of Pigs 28-day-old SPF pigs were selected for testing, and randomly divided into two groups with 5 pigs in each group. The two groups were inoculated with the recombinant virus A-T-r-PEVB and a DMEM/F12 medium (NC group), respectively. The day on which the first immunization was conducted was day 0, which was denoted as 0 dpi. The second and third immunization were conducted with the recombinant virus A-T-r-PEVB for pigs. The second immunization was conducted on day 14 after the first immunization, and the third immunization was conducted on day 21 after the first immunization. Each immunization was conducted through both intranasal administration and intramuscular injection. For the intranasal administration or intramuscular injection, each pig was inoculated at a dose of 1 mL of a virus solution with $10^{7.0}$ $TCID_{50}$/mL, such that each pig was inoculated each time at a total dose of 2 mL of a virus solution with a virus content of $10^{7.0}$ $TCID_{50}$/mL. For the NC group, each pig was inoculated with 2 mL of a DMEM/F12 medium each time.

Pigs inoculated with the recombinant virus A-T-r-PEVB were evaluated for immunogenicity. Serum IgG antibody expression levels against ASFV whole virus protein and ASFV p30, p22, p10, p54, cd2v-N, and B602L proteins before and after immunization were compared. A detection method of a serum antibody level against ASFV p30 could be seen in Xie Qinyun et al., 2023, Dynamics of Serological and Mucosal Antibody Responses against African Swine Fever Viruses in Experimentally Infected Pigs. Transboundary and emerging diseases, Article ID 9959847. Detection methods of serum antibody levels against other proteins were the same as the detection method of the serum antibody level against ASFV p30, except that only a coating protein was replaced with a corresponding protein. sIgA antibody levels in oral fluids before and after immunization were determined (a method was the same as the method in Xie Qinyun et al., 2023, Dynamics of Serological and Mucosal Antibody Responses against African Swine Fever Viruses in Experimentally Infected Pigs. Transboundary and emerging diseases, Article ID 9959847, except that a microplate plate was coated with ASFV p22 and p30 proteins in a protein concentration ratio of 2:1). Expression levels of cell-mediated immunity-associated and pro-inflammatory cytokines were determined by qPCR. A method for determining the expression levels of cell-mediated immunity-associated and pro-inflammatory cytokines by qPCR was as follows: Quantitative fluorescence primers for pro-inflammatory cytokines of pigs (shown in a table below) were designed. RNA was extracted from serum and then reverse-transcribed into cDNA using a reverse-transcription kit HiScript® III RT SuperMix for qPCR (+gDNA wiper) (purchased from Vazyme, Item No. R323-01). A β-actin gene was adopted as an internal reference control. A $2^{-\Delta\Delta CT}$ method (Livak and Schmittgen, 2001, Analysis of relative gene expression data using real-time quantitative PCR and the 2 (T) (-Delta Delta C) method. Methods 25, 402-408.) was used to determine fold changes in the mRNA expression of porcine cytokine genes between the immunization group and the NC group.

TABLE 6

Quantitative fluorescence primers for the pro-inflammatory cytokines of pigs

| Cytokine | Sense primer sequence (5'-3') | Antisense primer sequence (5'-3') |
| --- | --- | --- |
| TNF-α | CCAATGGCAG AGTGGGTATG (SEQ ID NO: 25) | TGAAGAGGAC CTGGGAGTAG (SEQ ID NO: 26) |
| IFN-α | GGCTCTGGTG CATGAGATGC (SEQ ID NO: 27) | CAGCCAGGAT GGAGTCCTCC (SEQ ID NO: 28) |
| IFN-γ | GCTCTGGGAA ACTGAATGAC (SEQ ID NO: 29) | TCTCTGGCCT TGGAACATAG (SEQ ID NO: 30) |
| IL-6 | ATCAGGAGAC CTGCTTGATG (SEQ ID NO: 31) | TGGTGGCTTT GTCTGGATTC (SEQ ID NO: 32) |
| IL-10 | GCATCCACT TCCCAACCA (SEQ ID NO: 33) | CTTCCTCATCT TCATCGTCAT (SEQ ID NO: 34) |

TABLE 6-continued

Quantitative fluorescence primers for the pro-inflammatory cytokines of pigs

| Cytokine | Sense primer sequence (5'-3') | Antisense primer sequence (5'-3') |
|---|---|---|
| IL-2 | AAGCACAGCAG CAGCAGCAG (SEQ ID NO: 35) | GCCGCAGAGGT CCAAGTTCATC (SEQ ID NO: 36) |
| β-actin | CATCACCAT CGGCAACGA (SEQ ID NO: 37) | GCGTAGAGGTC CTTCCTGATGT (SEQ ID NO: 38) |

T cell clustering was conducted for porcine PBMCs (a specific method could be seen in Chung CJ, Cha S-H, Grimm AL, Ajithdoss D, Rzepka J, Chung G, et al. (2018) Pigs that recover from porcine reproduction and respiratory syndrome virus infection develop cytotoxic CD4+CD8+ and CD4+CD8-T-cells that kill virus infected cells. PLOS ONE 13 (9): e0203482). The immunogenicity of the recombinant virus A-T-r-PEVB carrying the T cell epitope of ASFV in pigs was comprehensively evaluated.

Figure 23:
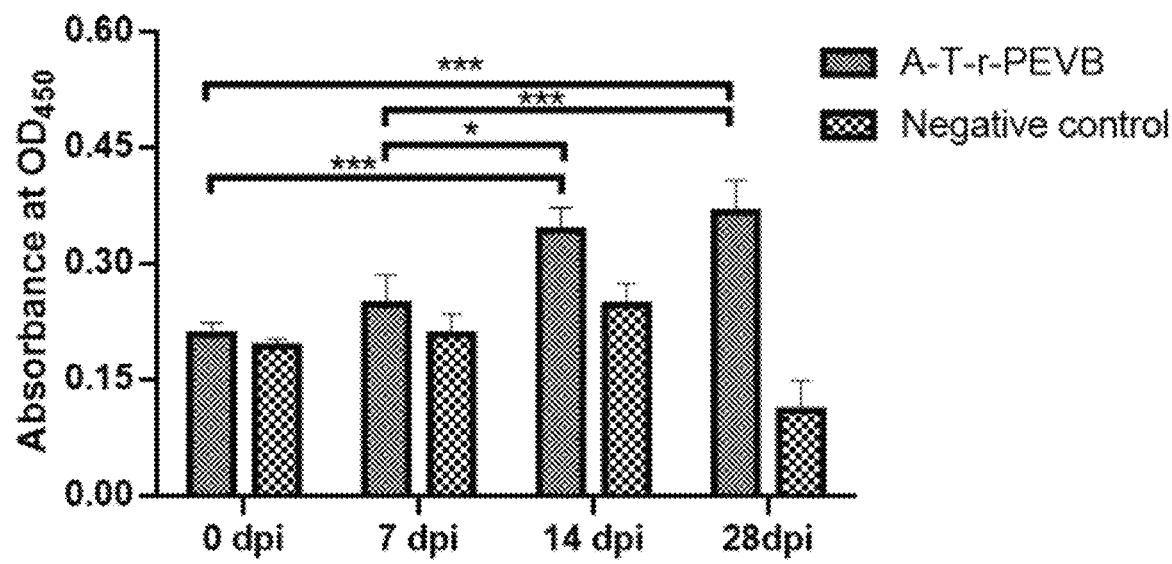
Figure 24:
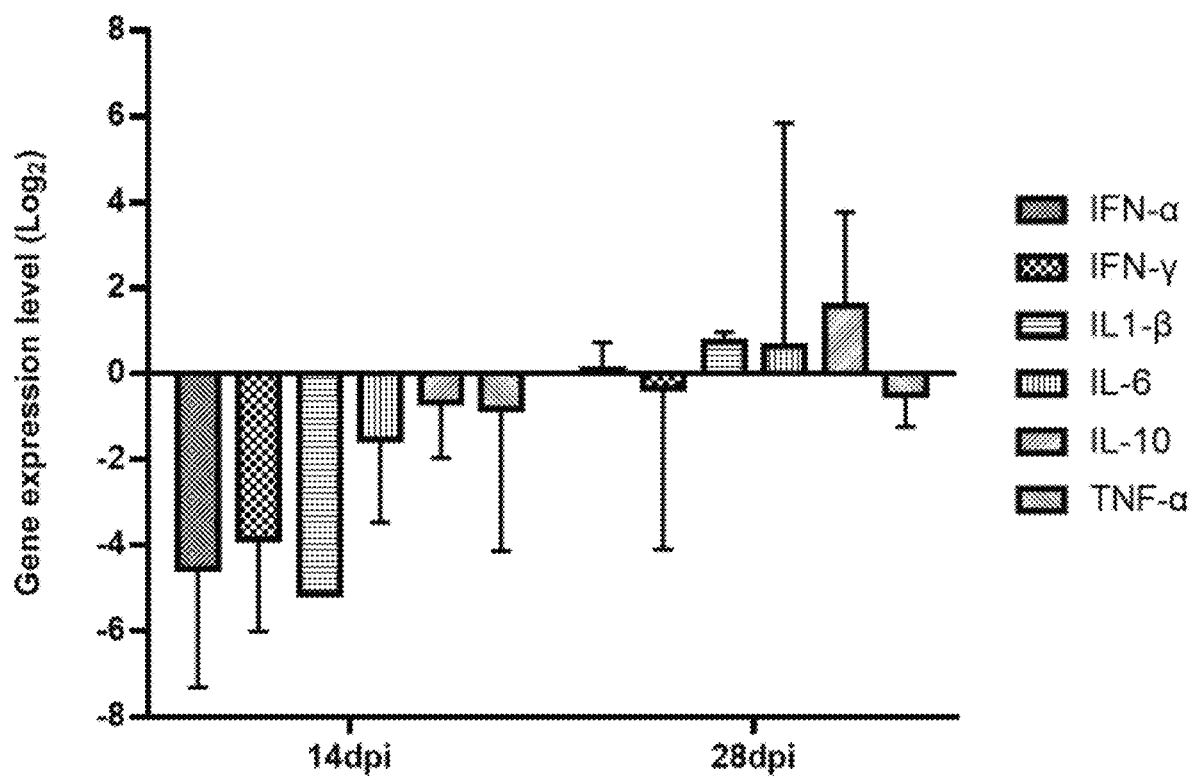
Figure 25:
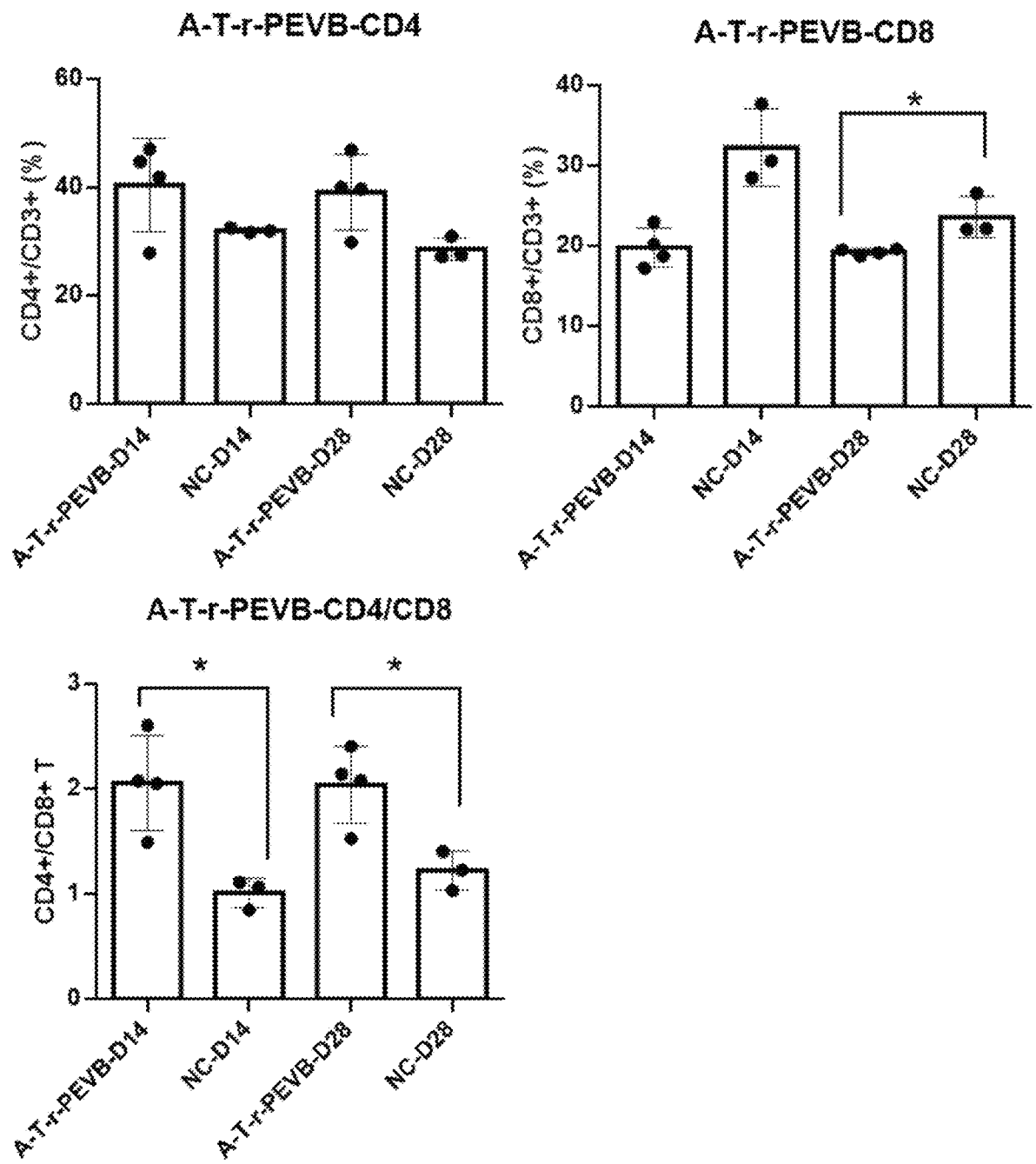

Results: Serum IgG antibody levels against the five antigens (CD2V-N, P10, P30, P54, and B602L) all were greatly improved on day 28 after immunization compared with the control group. A serum IgG antibody level against P22 was significantly increased on day 14 after immunization compared with the control group. Details were shown in FIGS. 22A-22F. sIgA antibody levels in oral fluids especially on day 14 and day 28 after immunization were significantly increased compared with the corresponding sIgA antibody level before immunization. Details were shown in FIG. 23. In terms of expression levels of inflammatory cytokines, compared with the NC group, the expression of IFN-α, IFN-γ, and IL-1B was significantly down-regulated on day 14 after immunization, and the expression of IL-10 was significantly up-regulated on day 28 after immunization. Details were shown in FIG. 24. Compared with the NC group, a percentage of CD8+CD3+ cells in PBMCs was significantly down-regulated on day 28 after the first immunization. On day 14 after the first immunization, a proportion of CD4+/CD8+ T cells in PBMCs was significantly up-regulated compared with the NC group. On day 28 after the first immunization, a proportion of CD4+/CD8+ T cells was significantly up-regulated compared with the NC group. It indicated that the recombinant virus A-T-r-PEVB could make an organism produce a CD4+ T cell-biased immune response by weakening the immunity of CD8+ T cells on day 28 after the first immunization. The above results all showed that the recombinant virus A-T-r-PEVB led to excellent immunogenicity of pigs after immunization.

(3) Immunogenicity of Pigs Immunized with the Recombinant Virus M-r-PEVB Against Mhp and Protective Efficacy Evaluation 28 d-old SPF pigs were randomly divided into three groups (immune challenge group, challenge control group, and NC group) with 5 pigs in each group. In the immune challenge group, three immunizations were conducted. The day on which the first immunization was conducted was day 0, which was denoted as 0 dpi. The second immunization was conducted on day 14 after the first immunization, and the third immunization was conducted on day 28 after the first immunization. Each immunization was conducted through both intranasal administration and intramuscular injection with 1 mL of an M-r-PEVB virus solution with a virus content of $10^{7.0}$ TCID$_{50}$/mL, and each pig was immunized with 2 mL of a virus solution with a virus content of $10^{7.0}$ TCID$_{50}$/mL in total. The NC group was immunized three times according to the same method as above, except that only the M-r-PEVB virus solution was replaced with a DMEM/F12 medium. In the immune challenge group, on day 42 after the first immunization, 5 mL of an Mhp 168 strain virus solution was administered through tracheal injection at a dose of $10 \times 10^{9.5}$ CCU/pig/time. In the NC group (denoted as a KM2 control group), three immunizations all were conducted by administering a KM2 liquid medium through tracheal injection with the same volume as the M-r-PEVB virus solution for each immunization, and no challenge was conducted. In the challenge control group, three immunizations all were conducted by administering a same volume of a KM2 liquid medium through tracheal injection, and on day 42 after the first immunization, an Mhp 168 strain was administered through tracheal injection for challenge at the same dose as the immune challenge group. During the whole test period, pigs in each group were observed every day for clinical symptoms such as cough of the respiratory tract. On day 28 after the challenge, namely, on day 70 after the first immunization, pigs were dissected. Lung lesions in the immune challenge group, the challenge control group, and the NC group after necropsy were scored (a scoring method could be seen in Madec F, Kobisch M, Bilaan Lesionnel des poumons des porcs chaarcutiers alab-attoir, Journees de la Recherche Porcine en France, 1982, 14:405-412.). Levels of a serum antibody against Mhp P97R1 and levels of a mucosal sIgA antibody in a BALF before immunization and after challenge were determined by ELISA (detection methods could be seen in Gan & Xie et al., 2020, Establishment of a model of *Mycoplasma* hyopneumoniae infection using Bama miniature pigsFood Production, Processing and Nutrition (2020) 2:19). Cilia of lungs before immunization and after challenge were observed under an electron microscope (a specific method could be seen in Gan & Xie et al., 2020, Establishment of a model of *Mycoplasma* hyopneumoniae infection using Bama miniature pigsFood Production, Processing and Nutrition (2020) 2:19). The immunogenicity and immune protection of pigs immunized with the recombinant virus M-r-PEVB against Mhp were comprehensively evaluated.

During the whole experimental process of challenged immunization, no pathological changes were found at an injection site, indicating that the recombinant virus M-r-PEVB is relatively safe when used as a candidate viral vector vaccine strain for Mhp.

Figure 26:
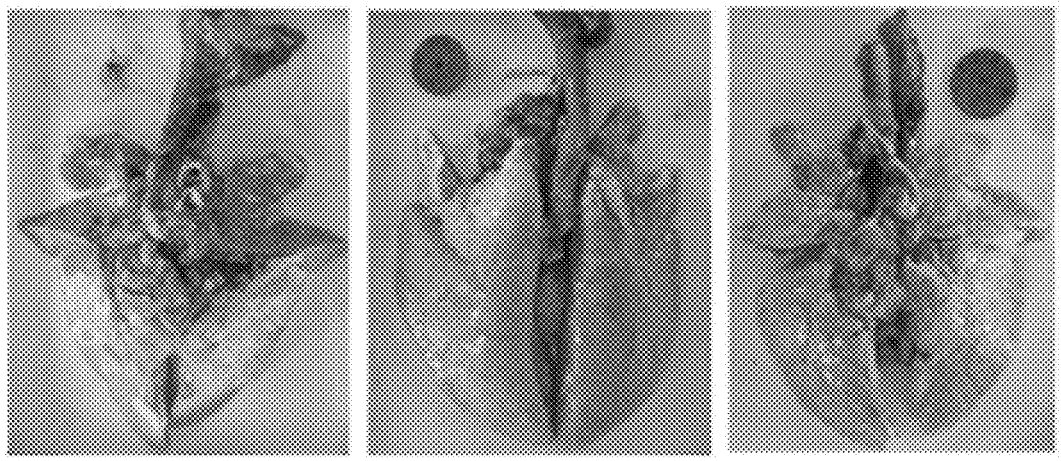
FIG. 26 shows apparent lesions in lungs collected from dissected pigs immunized with the recombinant virus M-r-PEVB.

According to results of apparent lesions in lungs after necropsy shown in FIG. 26: The challenge control group had very typical and strong Mhp lesions, with typical red to purple flesh lesions in apical lobes and interior lobes, which could have a score of 18 to 20 under 28-point scoring. There was a little difference between the immune challenge group and the NC group with scores of 3 and 0, respectively, indicating that M-r-PEVB can play a significant immune protection role in the immune challenge group.

Figure 27:
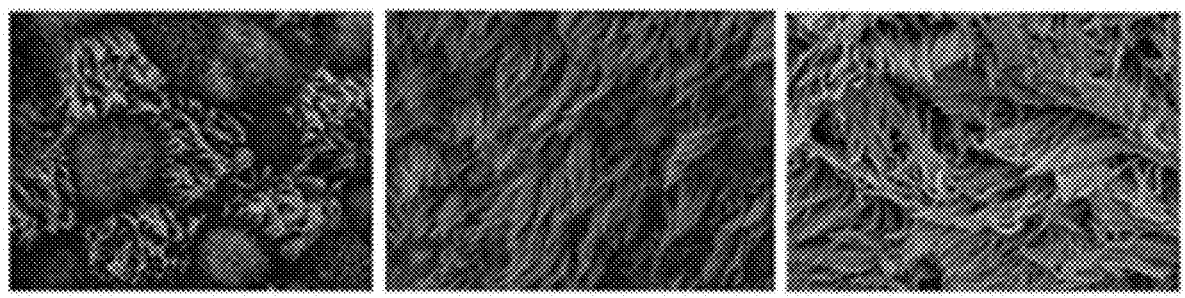
FIG. 27 shows electron microscopy observation results for bronchical cilium structures in pigs immunized with the recombinant virus M-r-PEVB.

After necropsy, a bronchial ring of each pig was cut, fixed with glutaraldehyde, and observed by electron microscopy for cilia. Results were shown in FIG. 27. In the challenge control group, 90% of bronchial cilia fell off, the ciliary morphology was no longer present, and the bronchial ring became bald. In the M-r-PEVB-immunized immune challenge group, about 5% to 10% of cilia also fell off, but the relatively-intact ciliary morphology was still retained. In the NC group, the very intact ciliary morphology was retained, and no cilia fell off.

Figure 28:
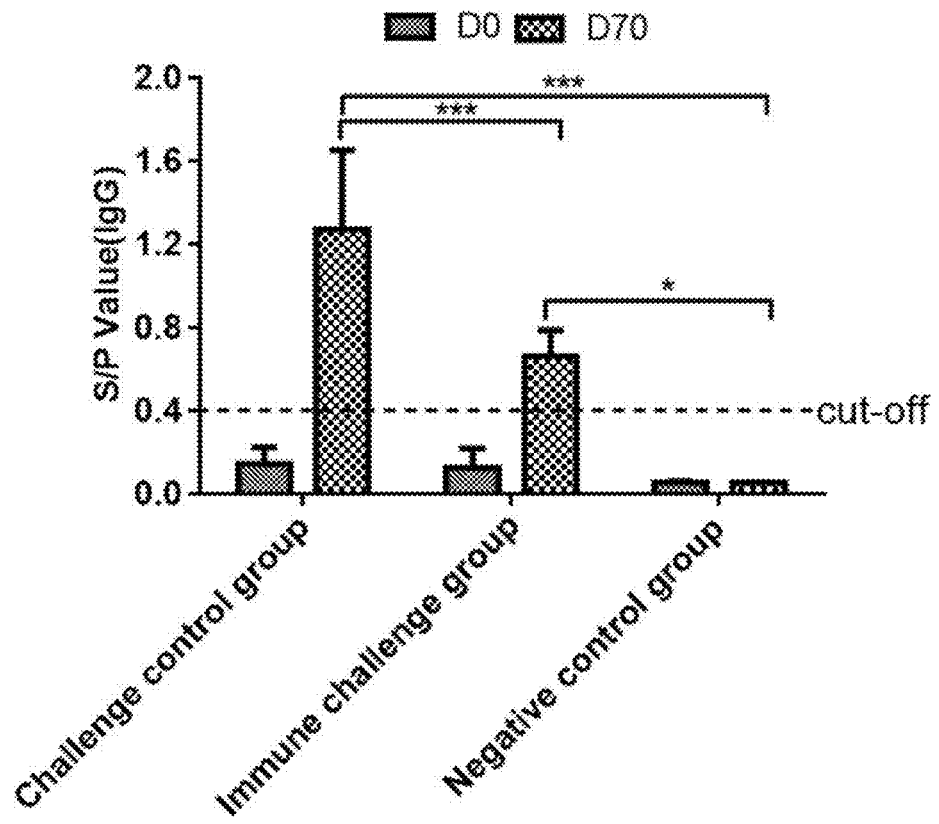
FIG. 28 shows serum IgG antibody levels in pigs immunized with the recombinant virus M-r-PEVB, where DO indicates sampling before the first immunization, D70 indicates sampling on day 70 after the first immunization (namely, after virus attack), "*" represents p<0.05 indicating a significant difference, and "***" represents p<0.01 indicating an extremely-significant difference.
Figure 29:
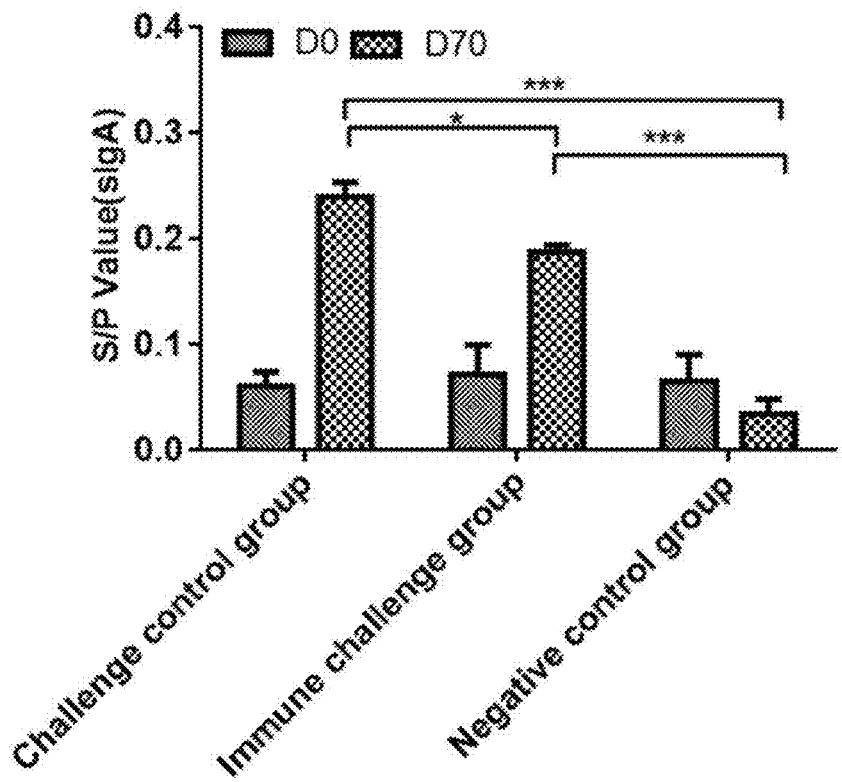
FIG. 29 shows sIgA antibody levels in mucosae of nasal swabs from pigs immunized with the recombinant virus M-r-PEVB, where DO indicates sampling before the first immunization, D70 indicates sampling on day 70 after the first immunization (namely, after virus attack), "*" represents p<0.05 indicating a significant difference, and "*" represents p<0.01 indicating an extremely-significant difference.

Before the first immunization and after the challenge, 3 mL of whole blood was collected from each pig to prepare serum, and a nasal swab was collected. A serum IgG antibody level against Mhp was detected, and a mucosal antibody sIgA level against Mbp in the nasal swab was detected. As shown in FIG. 28 and FIG. 29, serum IgG and mucosal sIgA antibody secretion levels in pigs of the immune challenge group were significantly higher than those in the NC group, where a difference in the mucosal antibody level was more significant than a difference in the serum antibody level. The above results showed that the M-r-PEVB-immunized immune challenge group did have a specified protective effect at an antibody level.

Figure 30:
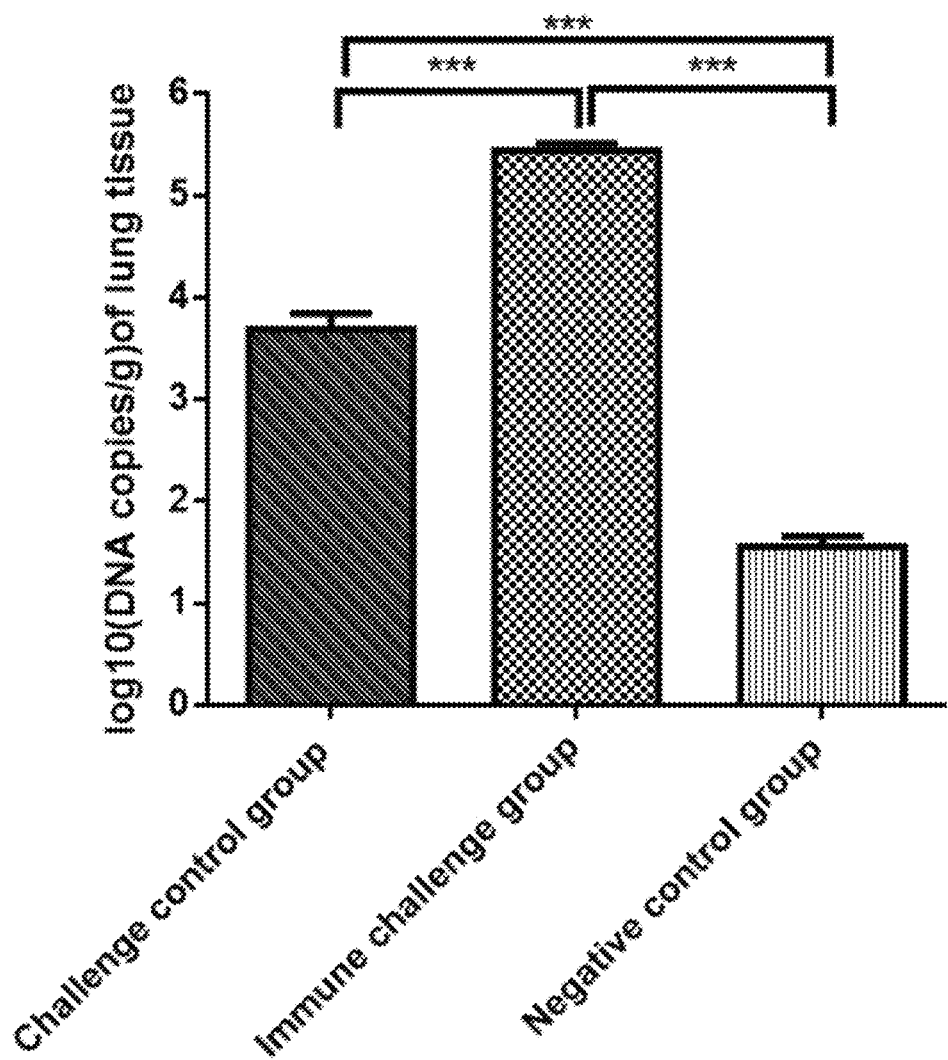
FIG. 30 shows DNA copy numbers of Mhp in bronchoalveolar lavage fluids (BALFs) from pigs immunized with the recombinant virus M-r-PEVB, where a y-coordinate represents a DNA copy number of Mhp in a lung tissue based on log 10, and "*" represents p<0.01 indicating an extremely-significant difference.

After necropsy, BALF of each pig was collected. Through a constructed standard positive plasmid PMD-T-P97 carrying an Mhp P97 antigen (a P97 sequence of an Mhp strain 168 (GeneBank accession number NC_017509.1) was inserted into a PMD-18T vector to finally produce the standard positive plasmid carrying the Mhp P97 antigen), an Mhp copy number in BALF of each pig was determined by quantitative fluorescence PCR. A specific detection method was shown in Wu, Y., Ishag, H. Z. A., Hua, L., Zhang, L., Liu, B., Zhang, Z., et al. (2019). Establishment and application of a real-time, duplex PCR method for simultaneous detection of *Mycoplasma* hyopneumoniae and *Mycoplasma* hyorhinis. Kafkas Universitesi Veteriner Fakultesi Dergisi, 25, 405-414. It can be seen from FIG. 30 that a DNA copy number in the immune challenge group was significantly lower than a DNA copy number in the challenge control group, and no Mhp was detected in the NC group. The results showed that the recombinant virus M-r-PEVB immunization exhibited a prominent protective effect for the infection of Mhp in pigs.

In summary, M-r-PEVB is safe when used as a recombinant viral vector expression strain for Mhp, and has a prominent immune protection effect against Mhp infection.

r-PEVB exhibits high safety when used as a vaccine vector for respiratory and gastrointestinal tracts, and has a prominent immune protection effect against Mhp and African swine fever virus.

What is claimed is:

1. A viral vector delivery system for both a respiratory tract and a digestive tract of a pig, comprising a backbone plasmid and a helper plasmid, wherein the backbone plasmid is produced by inserting a full-length cDNA of porcine enterovirus B (PEVB) having the nucleotide sequence of SEQ ID NO: 39 into a pUC57 plasmid, wherein SEQ ID NO: 2 or SEQ ID NO: 4 or SEQ ID NO: 6 is inserted between the VP4 and 5' UTR of the PEBV genome; and the helper plasmid is produced by inserting a green fluorescent protein-coding gene into a plasmid pCAG-T7-polymerase.

2. The viral vector delivery system according to claim 1, wherein a T7 promoter is inserted at a first terminus of the full-length cDNA of the SEQ ID NO: 39 in the backbone plasmid, and a his-tag and a polyA tail are inserted at a second terminus.

3. A construction method of the viral vector delivery system according to claim 1, comprising the following steps: constructing the backbone plasmid and the helper plasmid separately, and co-transfecting the backbone plasmid and the helper plasmid into monkey kidney cells or porcine bronchial epithelial cells.

4. The construction method according to claim 3, wherein a process for constructing the backbone plasmid is as follows: with a full-length cDNA of SEQ ID NO: 39 as a template, introducing a T7 promoter at a 5' terminus of the full-length cDNA of SEQ ID NO: 39 and a his-tag and a polyA tail at a 3' terminus through a polymerase chain reaction (PCR), and inserting into the pUC57 plasmid to produce the backbone plasmid.

5. The construction method according to claim 4, wherein a process for constructing the helper plasmid is as follows: inserting the green fluorescent protein-coding gene into the plasmid pCAG-T7-polymerase to produce the helper plasmid.

6. The construction method according to claim 5, wherein the backbone plasmid and the helper plasmid are co-transfected into monkey kidney cells veroE6 with a liposome nanoparticle transfection reagent, and a viral plaque producing green fluorescence is picked to produce the viral vector delivery system.

7. A method of constructing a vaccine antigen for a respiratory tract and a digestive tract of a pig comprising the steps of producing a backbone plasmid by inserting a full-length cDNA of porcine enterovirus B (PEVB) having the nucleotide sequence of SEQ ID NO: 39 into a pUC57 plasmid, wherein SEQ ID NO: 2 or SEQ ID NO: 4 or SEQ ID NO: 6 is inserted between the VP4 and 5' UTR of the PEBV genome; and producing a helper plasmid by inserting a green fluorescent protein-coding gene into a plasmid pCAG-T7-polymerase.

8. The method according to claim 7, further comprising: conducting co-transfection with the helper plasmid using a liposome nanoparticle transfection reagent into monkey kidney cells veroE6 or porcine bronchial epithelial cells hTERT-PBECs to produce the vaccine antigen.

* * * * *

SEQUENCE LISTING

```
Sequence total quantity: 39
SEQ ID NO: 1            moltype = AA   length = 216
FEATURE                 Location/Qualifiers
source                  1..216
                        mol_type = protein
                        organism = synthetic construct
SEQUENCE: 1
GGATCCGGGA TGCAAATGTC AAAAAATGTA GCTGGTAGCC ATACCACCGT TACCCAAGCG   60
ACGAACGGTA GCAAGATCCA CTACACCAAT ATTAACTATT ACAACCACAG CGCGTCGGCT  120
TCTCAGAATA AACAGGACAT CACTCAAGAC CCGAGCAAGT TCACCCAGCC GGTGGTGGAT  180
CTGATGAAAG AGAGCGCAGT TCCGTTGAAG CTCGAG                            216

SEQ ID NO: 2            moltype = DNA  length = 702
FEATURE                 Location/Qualifiers
source                  1..702
                        mol_type = other DNA
                        organism = synthetic construct
SEQUENCE: 2
gggcccatga aggccgctgc tatcgaggaa gaagatatcc agttcatcaa cccaggcggc   60
ggcggaagca cagtgaccac ccagaataca gcctcccaga ccatgagcgc catcggcggc  120
ggcgggagct ttatcggata tgttttcaag gccctgcaag agtggatgcc ttctggcggc  180
ggcggctctc tctctcaaca catccccccc caggatacat tttataagtg gaacggcgga  240
ggcggctcct acgtgtacaa caaccctcac caccctgtgc tgaagtacgg aggcggcgga  300
ggcagcagca agatcagcag ctgcgagttc accccctaact tctaccggtt cggcggcgga  360
ggcagcctgg cccagaaaac cgtccagcat atcgagcagt acggcaaggc cggcgggcga  420
ggatctaccg ccattaagac cctgctgtcc acagtgaaat acgacatcgt gggcggcggc  480
ggcacaagca gcttcgaaac cctgttcgag ggcggcggag gcagctacct gaacatcaac  540
gacaccttcg tgaagtacac caacgagtct atcctgaat acaactggaa tggcggcggc  600
ggaagccacg ccagctccag catgcacagc ggcatgctgt acaaggacat ggtgaacatc  660
gccagaagca gaggcatccc tatctaccag aatggcgggc cc                    702

SEQ ID NO: 3            moltype = AA   length = 232
FEATURE                 Location/Qualifiers
source                  1..232
                        mol_type = protein
                        organism = synthetic construct
SEQUENCE: 3
MKAAAIEEED IKYINPGGGG STVTTQNTAS QTMSAIGGGG SFIGYVFKAL QKEMPSGGGG   60
SLSQHIPPQD HYYKWNGGGG SYVYNNPHHP VLKYGGGGGS SKISSCEFTP NFYRFGGGGS  120
LAQKTVQHIE QYGKAGGGGS TAIKTLLSTV KYDIVGGGGT SSFETLFEGG GGSYLNDTIN  180
AFVKYTNESI LEYNWNGGGG SHASSSMSHG MILYKDMVNI ARPTHGYIYQ NG          232

SEQ ID NO: 4            moltype = DNA  length = 267
FEATURE                 Location/Qualifiers
source                  1..267
                        mol_type = other DNA
                        organism = synthetic construct
SEQUENCE: 4
gggcccatgc tgcctcagcc ccccgccgcc aagcagaag ctgccaaacc agtcgccgcc    60
aagcctgagg ccgccaagcc tgtggccgct aagcctgagg ccgctaagcc tgtggccgcc  120
aagcctgaag ccgcaaagcc tgtggccgcc aagcccgagg ccgccaaacc tgtggccgct  180
aaacctgtgg ctacaaacac caacacaaat accggcttca gcctgaccaa caagcccaag  240
```

```
gaggactact tccccatggc cgggccc                                          267

SEQ ID NO: 5            moltype = AA   length = 85
FEATURE                 Location/Qualifiers
source                  1..85
                        mol_type = protein
                        organism = synthetic construct
SEQUENCE: 5
MLPQPPAAKP EAAKPVAAKP EAAKPVAAKP EAAKPVAAKP EAAKPVAAKP EAAKPVAAKP       60
VATNTNTNTG FSLTNKPKED YFPMA                                            85

SEQ ID NO: 6            moltype = DNA   length = 972
FEATURE                 Location/Qualifiers
source                  1..972
                        mol_type = other DNA
                        organism = synthetic construct
SEQUENCE: 6
gggcccatga aagcagctgc gatagaggaa gaagatatcc agtttatcaa cccaggtggc       60
ggcggctcca ccgtaacgac ccaaaacacc gcaagtcaaa ccatgagcgc aatcggtggt      120
ggcggttcgt tcattggtta tgtctttaaa gcactgcaag aatggatgcc gtccggtggt      180
ggcggttcgc tctctcaaca catcccgcct caggacacgt tctacaaatg aatggtggc       240
ggcggctctt acgtttataa caacccgcat catccggttc tgaaatacgg cggtggcggt      300
ggctcctcca aaatcagctc ttgcgaattc accccgaact tttaccgttt tggtggtggt      360
ggtagcctgg ctcagaaaac ggtgcagcat atcgaacagt atggtaaggc gggtggcggc      420
ggctcaaccg cgatcaaaac tctgctgagc accgtgaaat atgatattgt tggtggcggc      480
ggcaccagct cgttcgagac attgtttgag ggaggagcg cagctactt aaatattaac        540
gacaccttcg tgaaatacac caatgaaagc attttggaat ataactgaa tggcggtggt       600
ggtagccacg caagctcttc catgcacagc ggtatgctgt ataaggacat ggttaatatc      660
gcccgtagcc gcggtattcc gatttaccaa acggtggcg cgggggtag catgctgccg        720
cagccgccgg cagcgaagcc ggaggcggcc aagccggtgg cggcgaagcc ggaggctgcg      780
aagccagttg ccgccaagcc ggaggcggct aagccggtcg ccgcgaaacc ggaggcggca      840
aagcctgtgg cggcgaagcc ggaggcggcg aagccggttg ctgctaagcc agtggcaacc      900
aacacgaaca ccaacactgg tttagcttta ccaataaaac cgaaagaaga ttacttcccg      960
atggcagggc cc                                                          972

SEQ ID NO: 7            moltype = AA   length = 322
FEATURE                 Location/Qualifiers
source                  1..322
                        mol_type = protein
                        organism = synthetic construct
SEQUENCE: 7
MKAAAIEEED IKYINPGGGG STVTTQNTAS QTMSAIGGGG SFIGYVFKAL QKEMPSGGGG        60
SLSQHIPPQD HYYKWNGGGG SYVYNNPHHP VLKYGGGGGS SKISSCEFTP NFYRFGGGGS      120
LAQKTVQHIE QYGKAGGGGS TAIKTLLSTV KYDIVGGGGT SSFETLFEGG GGSYLNDTIN      180
AFVKYTNESI LEYNWNGGGG SHASSSMSHG MILYKDMVNI ARPTHGYIYQ NGGGGGSMLP      240
QPPAAKPEAA KPVAAKPEAA KPVAAKPEAA KPVAAKPEAA KPVAAKPEAA KPVAAKPVAT      300
NTNTNGFSL TNKPKEDYFP MA                                               322

SEQ ID NO: 8            moltype = DNA   length = 48
FEATURE                 Location/Qualifiers
source                  1..48
                        mol_type = other DNA
                        organism = synthetic construct
SEQUENCE: 8
aataatacga ctcactatag ggttaaaaca gcctgtgggt tgttccca                    48

SEQ ID NO: 9            moltype = DNA   length = 46
FEATURE                 Location/Qualifiers
source                  1..46
                        mol_type = other DNA
                        organism = synthetic construct
SEQUENCE: 9
aatttttttt ttttttttac accccatccg gtgggtgtat tgaatt                      46

SEQ ID NO: 10           moltype = DNA   length = 25
FEATURE                 Location/Qualifiers
source                  1..25
                        mol_type = other DNA
                        organism = synthetic construct
SEQUENCE: 10
ttaataatac gactcactat agggt                                             25

SEQ ID NO: 11           moltype = DNA   length = 20
FEATURE                 Location/Qualifiers
source                  1..20
                        mol_type = other DNA
                        organism = synthetic construct
SEQUENCE: 11
ggaagaagac tgaagggttt                                                   20
```

```
SEQ ID NO: 12          moltype = DNA   length = 22
FEATURE                Location/Qualifiers
source                 1..22
                       mol_type = other DNA
                       organism = synthetic construct
SEQUENCE: 12
tgcagccaga tttagtgtac cg                                                22

SEQ ID NO: 13          moltype = DNA   length = 22
FEATURE                Location/Qualifiers
source                 1..22
                       mol_type = other DNA
                       organism = synthetic construct
SEQUENCE: 13
tcatcccaac tccaaagtcc at                                                22

SEQ ID NO: 14          moltype = DNA   length = 23
FEATURE                Location/Qualifiers
source                 1..23
                       mol_type = other DNA
                       organism = synthetic construct
SEQUENCE: 14
tcttggtgta atccaatctg cag                                               23

SEQ ID NO: 15          moltype = DNA   length = 24
FEATURE                Location/Qualifiers
source                 1..24
                       mol_type = other DNA
                       organism = synthetic construct
SEQUENCE: 15
ggctgctctt ttctcctaag tttt                                              24

SEQ ID NO: 16          moltype = DNA   length = 23
FEATURE                Location/Qualifiers
source                 1..23
                       mol_type = other DNA
                       organism = synthetic construct
SEQUENCE: 16
tctcatcact accctacgca ata                                               23

SEQ ID NO: 17          moltype = DNA   length = 20
FEATURE                Location/Qualifiers
source                 1..20
                       mol_type = other DNA
                       organism = synthetic construct
SEQUENCE: 17
tctcgtgatg ggacactaac                                                   20

SEQ ID NO: 18          moltype = DNA   length = 22
FEATURE                Location/Qualifiers
source                 1..22
                       mol_type = other DNA
                       organism = synthetic construct
SEQUENCE: 18
aagggaactc ttgaggttag at                                                22

SEQ ID NO: 19          moltype = DNA   length = 18
FEATURE                Location/Qualifiers
source                 1..18
                       mol_type = other DNA
                       organism = synthetic construct
SEQUENCE: 19
acgatcaagg gtccgact                                                     18

SEQ ID NO: 20          moltype = DNA   length = 45
FEATURE                Location/Qualifiers
source                 1..45
                       mol_type = other DNA
                       organism = synthetic construct
SEQUENCE: 20
ctcgacctgc agcccaagct tacataactt acggtaaatg gcccg                       45

SEQ ID NO: 21          moltype = DNA   length = 49
FEATURE                Location/Qualifiers
source                 1..49
                       mol_type = other DNA
                       organism = synthetic construct
SEQUENCE: 21
```

```
                                                     -continued
gaccatgatt acgccaagct ttaagataca ttgatgagtt tggacaaac              49

SEQ ID NO: 22           moltype = DNA   length = 20
FEATURE                 Location/Qualifiers
source                  1..20
                        mol_type = other DNA
                        organism = synthetic construct SEQUENCE: 22
aggctgactg gacggggcaa                                              20

SEQ ID NO: 23           moltype = DNA   length = 20
FEATURE                 Location/Qualifiers
source                  1..20
                        mol_type = other DNA
                        organism = synthetic construct SEQUENCE: 23
gcgccttggg aaacgacgag                                              20

SEQ ID NO: 24           moltype = DNA   length = 25
FEATURE                 Location/Qualifiers
source                  1..25
                        mol_type = other DNA
                        organism = synthetic construct SEQUENCE: 24
ctaccgttct cgttctagct ggccg                                        25

SEQ ID NO: 25           moltype = DNA   length = 20
FEATURE                 Location/Qualifiers
source                  1..20
                        mol_type = other DNA
                        organism = synthetic construct SEQUENCE: 25
ccaatggcag agtgggtatg                                              20

SEQ ID NO: 26           moltype = DNA   length = 20
FEATURE                 Location/Qualifiers
source                  1..20
                        mol_type = other DNA
                        organism = synthetic construct SEQUENCE: 26
tgaagaggac ctgggagtag                                              20

SEQ ID NO: 27           moltype = DNA   length = 20
FEATURE                 Location/Qualifiers
source                  1..20
                        mol_type = other DNA
                        organism = synthetic construct SEQUENCE: 27
ggctctggtg catgagatgc                                              20

SEQ ID NO: 28           moltype = DNA   length = 20
FEATURE                 Location/Qualifiers
source                  1..20
                        mol_type = other DNA
                        organism = synthetic construct SEQUENCE: 28
cagccaggat ggagtcctcc                                              20

SEQ ID NO: 29           moltype = DNA   length = 20
FEATURE                 Location/Qualifiers
source                  1..20
                        mol_type = other DNA
                        organism = synthetic construct SEQUENCE: 29
gctctgggaa actgaatgac                                              20

SEQ ID NO: 30           moltype = DNA   length = 20
FEATURE                 Location/Qualifiers
source                  1..20
                        mol_type = other DNA
                        organism = synthetic construct SEQUENCE: 30
tctctggcct tggaacatag                                              20

SEQ ID NO: 31           moltype = DNA   length = 20
FEATURE                 Location/Qualifiers
source                  1..20
                        mol_type = other DNA
                        organism = synthetic construct
```

-continued

```
SEQUENCE: 31
atcaggagac ctgcttgatg                                              20

SEQ ID NO: 32           moltype = DNA   length = 20
FEATURE                 Location/Qualifiers
source                  1..20
                        mol_type = other DNA
                        organism = synthetic construct
SEQUENCE: 32
tggtggcttt gtctggattc                                              20

SEQ ID NO: 33           moltype = DNA   length = 18
FEATURE                 Location/Qualifiers
source                  1..18
                        mol_type = other DNA
                        organism = synthetic construct
SEQUENCE: 33
gcatccactt cccaacca                                                18

SEQ ID NO: 34           moltype = DNA   length = 21
FEATURE                 Location/Qualifiers
source                  1..21
                        mol_type = other DNA
                        organism = synthetic construct
SEQUENCE: 34
cttcctcatc ttcatcgtca t                                            21

SEQ ID NO: 35           moltype = DNA   length = 20
FEATURE                 Location/Qualifiers
source                  1..20
                        mol_type = other DNA
                        organism = synthetic construct
SEQUENCE: 35
aagcacagca gcagcagcag                                              20

SEQ ID NO: 36           moltype = DNA   length = 22
FEATURE                 Location/Qualifiers
source                  1..22
                        mol_type = other DNA
                        organism = synthetic construct
SEQUENCE: 36
gccgcagagg tccaagttca tc                                           22

SEQ ID NO: 37           moltype = DNA   length = 18
FEATURE                 Location/Qualifiers
source                  1..18
                        mol_type = other DNA
                        organism = synthetic construct
SEQUENCE: 37
catcaccatc ggcaacga                                                18

SEQ ID NO: 38           moltype = DNA   length = 22
FEATURE                 Location/Qualifiers
source                  1..22
                        mol_type = other DNA
                        organism = synthetic construct
SEQUENCE: 38
gcgtagaggt ccttcctgat gt                                           22

SEQ ID NO: 39           moltype = DNA   length = 7393
FEATURE                 Location/Qualifiers
source                  1..7393
                        mol_type = genomic DNA
                        organism = Enterovirus G
SEQUENCE: 39
ttaaaacagc ctgtgggttg ttcccaccca cagggcccac tgggcgctag tacactggta    60
tgccttacct cggtatcacg gtaccgttgt atacagtacc tttgtacgcc tgttttaaat   120
cccctccccc caatgtaact ttagaagttt aagcaaacaa agaccaatag gagtccaaca   180
accagttgga ttgcggtcaa gcacttctgt ctccccggac ctagtagtga taggctgtac   240
ccacggccga agatgaaacc gtccgttacc cggccagcta cttcgagaag cctagtaaca   300
tcaaagatct gtcttggcgt ttcgctcagc gcgttccccc cgcgtagatc gggctgatgg   360
gtctccgcat accccacggg cgaccgtggc ggaggccgcg tggcggcccg cctatggcga   420
aagccatagg acgccatttc agtgacaggg tgtgaagagc ctattgagct agttggtagt   480
cctccggccc ctgaatgcgg ctaatcctaa ccacggagcg tccaccagca aaccagctgg   540
cagggcgtcg taacgggtaa ctctgtggcg gaaccgacta ctttgggtgt ccgtgtttcc   600
ttttgatcct atattggctg cttatggtga caacgataag ttgttatcat aaagcttttg   660
ggttggccac ctgaaaaaag ttatcagtgt ttgatattgt tcggctttca cgcctaccaa   720
taaaacaatc cttatattat tgatttcct tttatccaca agaggaaatt tctgagtttc   780
atctccagtt gctcttaacc ttatcagcaa gatgggtatg caaatgagca aaaacgttgc   840
```

```
cgggtcccat accaccgtga cacaagcaac caacggatcc aagatccact acactaacat   900
caattactac aaccactccg ctagtgctag tcaaaataag caggacatca cacaagatcc   960
tagcaagttc acacaaccag tggttgattt gatgaaggag tctgccgttc cattaaaatc  1020
accatcagcg gaagcatgtg gttacagtga cagaatcgca caacttacac ttggaaacag  1080
cacgataacc acacaagagg ctgctaacat cactgttgct tacggtgagt ggcccgaata  1140
tctttctgat caggatgcca ctgctgtcga caagaccacc aaaccaggtg tggcgtgtga  1200
ccgcttctac acgcttcctg gaaagaaatg gacagcagat gataaaggct gggaatggaa  1260
attaccagat gcacttactg agcttggagt ctttggacaa aactgccaat atcactactt  1320
aatgaggtgt gggtggacca ttcatgtgca gtgtaacgcc accaaatttc atcaaggctg  1380
tctgcttgtt gttgcagtac cagatcacca actgggcacc acgtataatc ctagctttga  1440
cgagaccatg ccagggaaga gtggtagaac tattaaatac ccatttgagt ttgaggatgg  1500
aactagtttg gcaaatgccc ttgtttaccc acaccagtgg atcaatatca gaaccaacaa  1560
ctcagctact ttagttctgc cctacataaa ttcaattcct atggactcag ccattcgtcg  1620
cagcaactgg tcgcttatgg tgataccatt agttccattg aaggccgcaa caggtaccac  1680
acctttgtg ggaattacag tgacagtagc accaatgatg tccgagttct cagggctacg  1740
caaagccatt gttcagggaa tccccactac aaacacccca ggttcatatc agttcatgac  1800
aacagatgag gactctagtg cttgcatgct tccagacttt actcctacac aagaaatcca  1860
cattccagga gaggtgaaaa atcttccagg ctttatgccag gtggagtcca ttatggaaat  1920
caataatgtt gaaggaaagt caggagttga aaggcttagc cttgaaatca gtgctcagac  1980
agatttggat agacaactct ttgcactaga agtaactttc aaacaggatt ccatcatgtc  2040
caaaactttg tgtggcatag tatgcagtta cttcactcaa tggtctggct ctcttgaaat  2100
taccttcatg tttactggat cctttgtgag tacaggaaaa ttgctgcttg cttacacacc  2160
accaggtggt gcggcaccaa caagcggga agatgccatg cttggtacac acgttgtgtg  2220
ggactttggg ttgcaaagtt caattactct agttataccaa tggatttgtg gaggatacta  2280
cagagacgtg gctagggcat ccaactacta cgcatccggc tacgttactg gatggtacca  2340
gaccaacctg gtcattcctc caaattttccc cacaactgtc acattgtgt gcttgctaga  2400
tgcacagcca aacttttcca tgagaataat gaaggacaga cccgacatta cccaaactgc  2460
tagactggaa gctcccattc agaatgctgt cgaaaatgcc attgtttctg ccattggaaa  2520
cgcaacggca gccgatactc agcaaagctc acacaacatt tccaccgcaa acactccagc  2580
tttacaggca gcagaaactg gagcccactt cactgctagt gatgaaggta tgcttgaaac  2640
cagacacgtt gttaatacaa acactgtctc tgagtcttcc gtggaaagct tttatgaag  2700
atctggactt gtttccatta ttgaacttgg agctggcaat gttgaaagc attggcttat  2760
taatttaat gagtttgtgc aaatgagagc aaagatggaa ttgtttacct acatgaggta  2820
tgcatcgag tttacgctag ttgccaccct tgtgaaagat ggtagtcgtt caaccccaca  2880
agtccaattg caagttatgt atgtgccacc tggtgccact acacctgaag atcaagactc  2940
gtaccaatgg cagtctgcag caaacccttc agtcttcttc caagcaaatg gtgttgcagc  3000
cagatttagt gtaccgttta tgggaacctc aaacgcatat gctatattct atgatggtta  3060
caacaccttt ggatccgatc gggcaggctc agattatggt aagattaaca gcagccatat  3120
gggtcacatt gcagttcgcg ctgtcgcgcc actcaagact ggagaggccg tcaccttgag  3180
ggtgtatgcc aaaccaaaac atgtcagagc atgggcaccc cgctccccaa ggatagctcc  3240
atatgtacgc atagcaaccc cagtgtttgg agctcgcaca aagaacgttc cagacaggac  3300
aaaatgtacta accaccactg gagcctttgg tcaacagagc ggagcagtat atgtgggcaa  3360
ctacaaaaata gtgaacaggc atcttgctac ccacgagaat gttgagtggga agttacaaac  3420
agattacaac agagatttgc ttgttgccag aaccactgcc cacggtgccg acaagctcgc  3480
cagatgtcac tgtaatgcag gtgtttacta ctgcaaatct agaaacaagc attatccagt  3540
cacccttcca ggaccaggta ttgattggat tgaagccagt gagtattacc cagccagata  3600
ccaaacccac cttcttcttg cttctggtat tctgaacca ggagactgtg gaggaatcct  3660
tagatgccag catggagtaa ttggaattgt taccgctgga ggtcaggag tagtcggttt  3720
tgctgacgtt agagaccttt tctgggttga gcatgaagcg atggaacagg tcttactgaa  3780
ctacatccaa cagcttggca acagctttgg acaaggcttc acagcagaaa ttaccaacta  3840
tgccagccag cttactgaga tgctcattgg agcagacgga atggtagaga ggtgcttaca  3900
gacttttgta aaagtgattt cagccattgt gattgcaacc agatcccaag gggatgtgcc  3960
aactattctt gcaactctcg cactcatcgg tgtgatggg agtccctgga gatgcttaa  4020
acgccaattt gcggaatct ttaaaatccc ctatgttgag aaacaaggag atgattggct  4080
aaagaagttt acatcctatg tcaacgcttt taagggactt gactgggtg cagagaagat  4140
tctcaaattt attgattgga tgaagaacaa gctgatcccc caggccagag aaagacaaga  4200
gtttgttaca aaccttaaaa ctttgcctct gctggaagct caagttgcta ccttggagca  4260
ctcgtgccca actacagaac aacaggagac catcttcggg aacattcagt acttggctca  4320
ccattgcaga agatatgccc cattgtatgc agctgaagcc agaagggtgt atgcccttga  4380
gaagagaatt ttaggataca tacagttcaa gagcaagcaa cgtattgaac ctgtctgcct  4440
cctaattcat ggtactgctg gtactggaaa atcattggct acttctatca ttggtagaaa  4500
acttgcagag tatgaacatt ctgaagtgta cgctgtgcct ccagatagtg accatttga  4560
tggataccag cagcaagctg tagttgttct ggatgaccta aaccaaaacc cagatggtaa  4620
agacatggtt gcttttttgtc agatggttctc aactgtacca tcacgtgcc ccatggatac  4680
tcttgaaag aagggaatgc ttttcaccag ctcccttgtt ttggcttcca caaacagtgg  4740
atctatccac ccaccaaccg tgtctaatgc caaagctcta tctaggagat ttgcgtttga  4800
tgtggacatt gaagtctcag aacattacaa aaatcacaat ggcactctca atgttgttga  4860
agctacccag aaatgtgatg attgttgtcc agcaaatttt aaaacttgca tgccttttaat  4920
ctgtggagaa gcttaccaac ttgtagatag aaggaagtact ccattgatac  4980
tatgatttca gcaatgagag cagagtggaa gagaaggaac caggtcggat ctgtcattga  5040
agctctgttc caaggaccc cagtgttcaa gccactcaaa atctcagtgg accccgagac  5100
accagcacca ccagctattg ctgatctttt ggctagcgtt gattctgaag aagtcagaga  5160
gtattgcaag aggaagggat ggattgtaga ggtaccagtg acagcaacca cccttgagag  5220
gaatgcttga attgcaacta ccatttttatc tagtttggtt cttttgacct ctgtcatcac  5280
tttggtatac ctggtatacc gactcttcgc tggttaccaa ggcccataca caggattgcc  5340
aaatgccaaa cccaagccac cagtacttag agaagtgaga gctcagggtc ctttgatgga  5400
cttttggagtt gggatgatga agaagaacat agtcacagta agaactgggg ctggtgaatt  5460
cactggcctt ggtgtctatg atcgtgtcct tgttctacca aaacattcac acccagctga  5520
gatagttgtg gttgacggga agagacagc agttgaggat gcgtacaact tgactgatga  5580
```

-continued

```
agagggtgtg tctctggagc tcacacttgt cactcttaaa agaaatgaga agtttaggga    5640
catcagagca atgattccag tgaatccctg tggtactaat gaagcagttg tgtgcgtgaa    5700
caccagtaat tttccaaatg ccttcttacc tgtaggtaaa gtggaatatt atggatacct    5760
caaccttgcg ggaagtccaa cgcaccgcac catgatgtat aacttcccca ccaaagcagg    5820
acagtgtggt ggtgtggttt tgtctactgg aaaagtgcta ggaatccaca tcggtggcaa    5880
tggagctcaa ggcttctgtg ccgcactgaa aagatcctac ttcacaaagc cacaaggtga    5940
gattgaaaag atggaaccat ccaagaagtc aggataccct gtgataaatg caccaactaa    6000
gactaagtta gaacccagtg ttttctttga tgtatttgaa ggggttaagg aacccgcagt    6060
tctccaccca aaagattccc gacttgaggt caacttagag gaggctctct tttctaagta    6120
tacaggtaat gttgacattg agatgcctga agaaatgaag gaagctgtgg accactatgc    6180
caaccaatta ctagctcttg acatttgcac cgaaccctg accatggatg aagccattta     6240
tggaactgaa ggtttggaag ctttagattt gactactagt gctggttacc cctacgtcac    6300
catgggaatt aagaagaaag acattcttaa caaggaaact agagatacca agaagatgca    6360
agagtgtatt gacaaatatg ggctcaacct tccgatggtg acctacatta aagatgagct    6420
tagatccaaa gaaaaggtga agaagggaaa aagcagatta attgaagcat ctagcttaaa    6480
tgactctgtt gccatgaggt gttattttgg aaatttatac aaagctttcc accaaaaccc    6540
aggcaccctg actgggtgtg ctgttggttg tgatccagac accttttgga gcaagattcc    6600
agtcatgatg gatggagaac ttttggatt tgattacacc gcctatgacg ccagtttgtc     6660
acccgtcatg tttgaagccc ttcagatggt tcttgagaaa attggatttg gtgacggaaa    6720
acagttatc caaaacctct gttattcaaa acacctgttc agagacaagt attaccttgt     6780
taagggagga atgccatcag gttgctctgg aaccagcatt tttaattcaa tgattaacaa    6840
cataataatt agaactgttg tccttcaaac ttataaagga attgaattgg atcagttgaa    6900
aattattgcg tatggggatg atgtgattgc cagttaccca tacagaatcg acccagctga    6960
attggccaag gctggggcga aactgggtct acacatgaca ccaccagaca agtctgatac    7020
ctatgtggac ctggactgga caaatgttac atttctgaag agaaactttg ttccagatga    7080
gaaataccca tttcttgtgc atccggttat gccaatgaaa gagattcacg aatctatcag    7140
gtggaccagg gatgcacgca acacacaaga tcacgtgcgt tctctgtgcc tgcttgcttg    7200
gcataatggc aaagaggagt atgagaactt ctgccgcaag atcagatcag taccagtcgg    7260
cagagctctt catttaccat cttactcctc actgctgcga gaatggtatg agaaatttta    7320
gattacagtt caattgatta tccggatcgg ccaaagcttc aattggattc aatacaccca    7380
ccggatgggg tgt                                                      7393
```